United States Patent
Abood et al.

[11] Patent Number: 6,025,358
[45] Date of Patent: Feb. 15, 2000

[54] DOUBLE PRODRUGS OF POTENT GP IIB/IIIA ANTAGONISTS

[75] Inventors: Norman Anthony Abood; Michael J. Bennett, both of Morton Grove; Lori A. Schretzman, Gurnee, all of Ill.

[73] Assignee: G. D. Searle & Co., Chicago, Ill.

[21] Appl. No.: 09/314,753

[22] Filed: May 19, 1999

Related U.S. Application Data

[60] Provisional application No. 60/088,996, Jun. 11, 1998.
[51] Int. Cl.[7] .................. A61K 31/40; A61K 31/495; C07D 403/12; C07D 207/24
[52] U.S. Cl. .................. 514/252; 514/424; 544/372; 548/550
[58] Field of Search .................. 514/252, 424; 544/372; 548/550

[56] References Cited

U.S. PATENT DOCUMENTS

| | | | |
|---|---|---|---|
| 5,344,957 | 9/1994 | Bovy et al. | 560/35 |
| 5,484,946 | 1/1996 | Abood et al. | 548/543 |
| 5,576,447 | 11/1996 | Abood et al. | 548/550 |
| 5,610,296 | 3/1997 | Abood et al. | 548/546 |
| 5,721,366 | 2/1998 | Abood et al. | 546/292 |

OTHER PUBLICATIONS

J. Med. Chem., vol. 39, Weller et al., pp. 3139–3147, 1996.
Pharmazie, vol. 43, Hauptmann et al., pp. 559–560, 1988.

*Primary Examiner*—Joseph K. McKane
*Attorney, Agent, or Firm*—Cynthia S. Kovacevic

[57] ABSTRACT

The present invention relates to double prodrugs of pharmacologically active glycoprotein IIb/IIIa antagonists of the formula

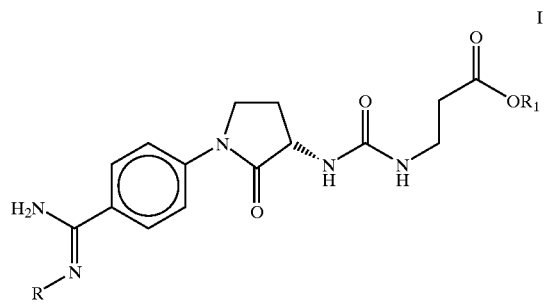

wherein $R_1$ is selected from the group consisting of lower alkyl of about 2 to about 8 carbon atoms, cycloalkyl, and aralkyl; R is selected from the group consisting of alkoxy,

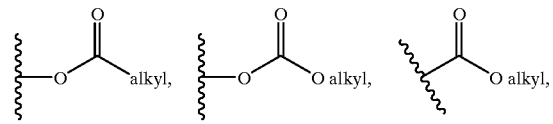

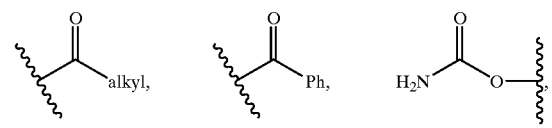

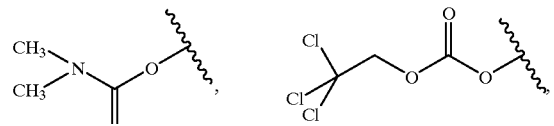

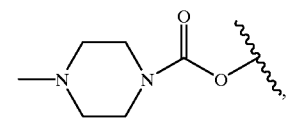

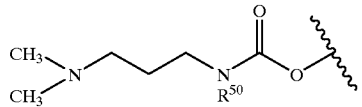

wherein $R^{50}$ is H or alkyl; and

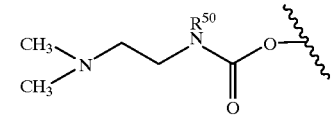

wherein $R^{50}$ is H or alkyl; and pharmaceutically acceptable salts thereof.

8 Claims, 1 Drawing Sheet

DOUBLE PRODRUGS OF POTENT GP IIB/IIIA ANTAGONISTS

The present application claims priority under 35 USC §119(e) of U.S. Provisional Patent Application Ser. No. 60/088,996 filed Jun. 11, 1998.

FIELD OF THE INVENTION

The present invention relates to double prodrugs of pharmacologically active glycoprotein IIb/IIIa antagonists.

BACKGROUND OF THE INVENTION

Fibrinogen is a glycoprotein present as a normal component of blood plasma. It participates in platelet aggregation and fibrin formulation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as GP IIb/IIIa; this is an important feature of the platelet function. Inhibitors of this interaction are useful in modulating platelet thrombus formation.

It is also known that another large glycoprotein named fibronectin, which is a major extracellular matrix protein, interacts with platelets. Various relatively large polypeptide fragments in the cell-binding domain of fibronectin have been found to have cell-attachment activity. Certain relatively short peptide fragments from the same molecule were found to promote cell attachment to a substrate when immobilized on the substrate or to inhibit attachment when in a solubilized or suspended form.

U.S. Pat. No. 5,721,366 is directed to a class of compounds of the formula

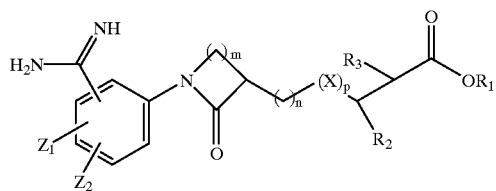

which are useful as modulators and/or inhibitors of platelet aggregation. Included in this class of compounds is a compound of the formula

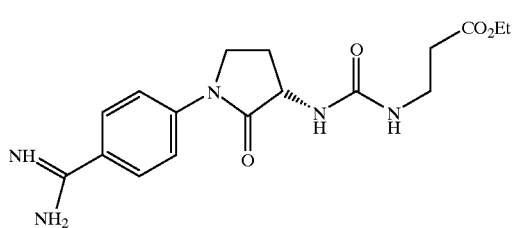

generically known as orbofiban, chemically known as N-[[[1-[4-(aminoiminomethyl)phenyl]-2-oxopyrrolidin-3S-yl]amino]carbonyl]-β-alanine.

U.S. Pat. No. 5,610,296 discloses compounds of the formula

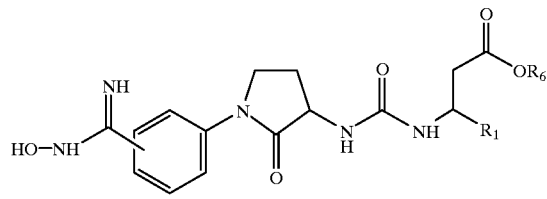

wherein $R_1$ is selected from the group consisting of H, lower alkyl, and aryl; and wherein $R_6$ is selected from the group consisting of lower alkyl, aryl, arylalkyl and acyloxymethyl.

U.S. Pat. No. 5,344,957 is directed to GP IIb/IIIa antagonists of the formula

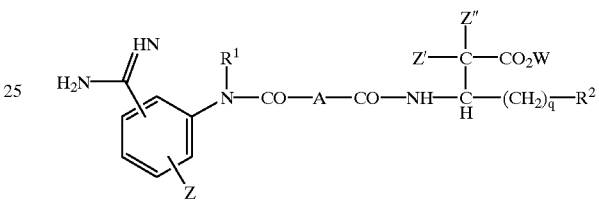

which are useful as modulators and/or inhibitors of platelet aggregation. Included in this class of compounds is a compound of the formula

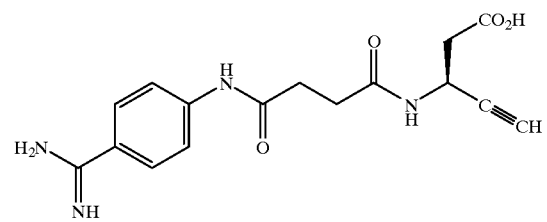

generically known as xemilofiban and chemically known as ethyl 3S-[[4-[[4-(aminoiminomethyl)phenyl]amino]-1,4-dioxobutyl]amino]-4-pentynoate.

Bioconversion of amidoxime prodrugs to amidines has been disclosed and occurs via hepatic metabolism [Hauptmann, J. et al. Pharmazie 43, 559–560 (1988)]. European Patent Application 656,348 A2 discloses double prodrugs of a series of glycoprotein IIb/IIIa antagonists. The compounds are further disclosed in Weller, T. et al. J. Med. Chem. 39, 3139–3147 (1996).

SUMMARY OF THE INVENTION

The present invention relates to double prodrugs of pharmacologically active glycoprotein IIb/IIIa antagonists of the formula

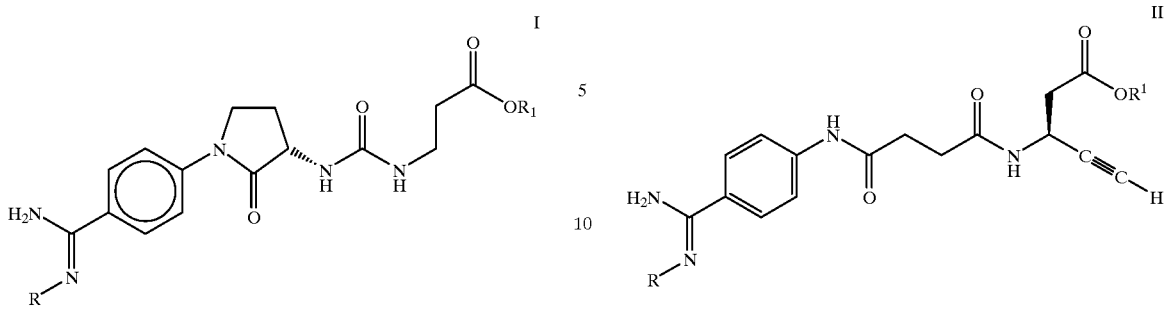

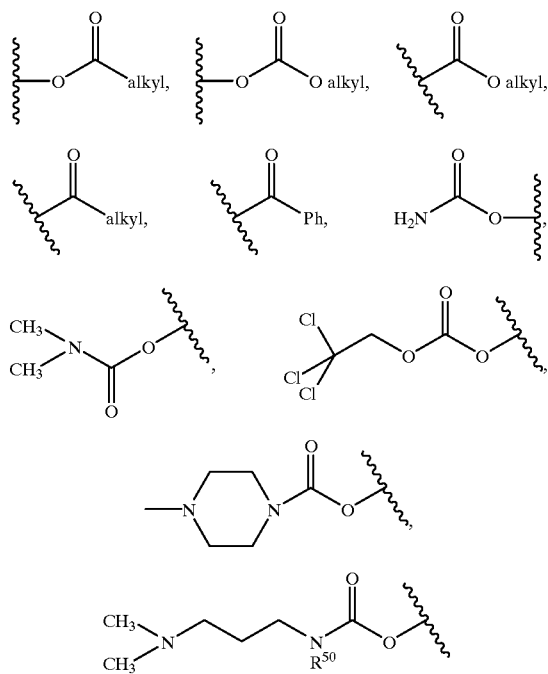

wherein $R_1$ is selected from the group consisting of lower alkyl of about 2 to about 8 carbon atoms, cycloalkyl, and aralkyl; R is selected from the group consisting of alkoxy,

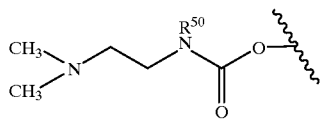

wherein $R^{50}$ is H or alkyl; and pharmaceutically acceptable salts thereof.

In another embodiment the present invention relates to double prodrugs of pharmacologically active glycoprotein IIb/IIIa antagonists of the formula

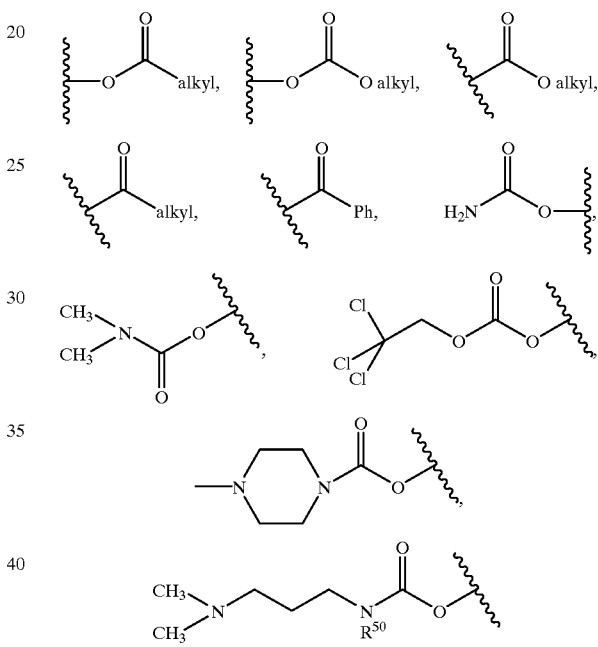

wherein $R_1$ is selected from the group consisting of H, lower alkyl of about 2 to about 8 carbon atoms, cycloalkyl and aralkyl; R is selected from the group consisting of OH, alkoxy,

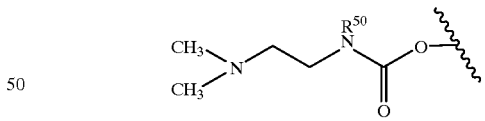

wherein $R^{50}$ is H or alkyl; and wherein $R^{50}$ is H or alkyl; and pharmaceutically acceptable salts thereof.

It is another object of the invention to provide pharmaceutical compositions comprising compounds of the formulae I and II. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

Figure 1:
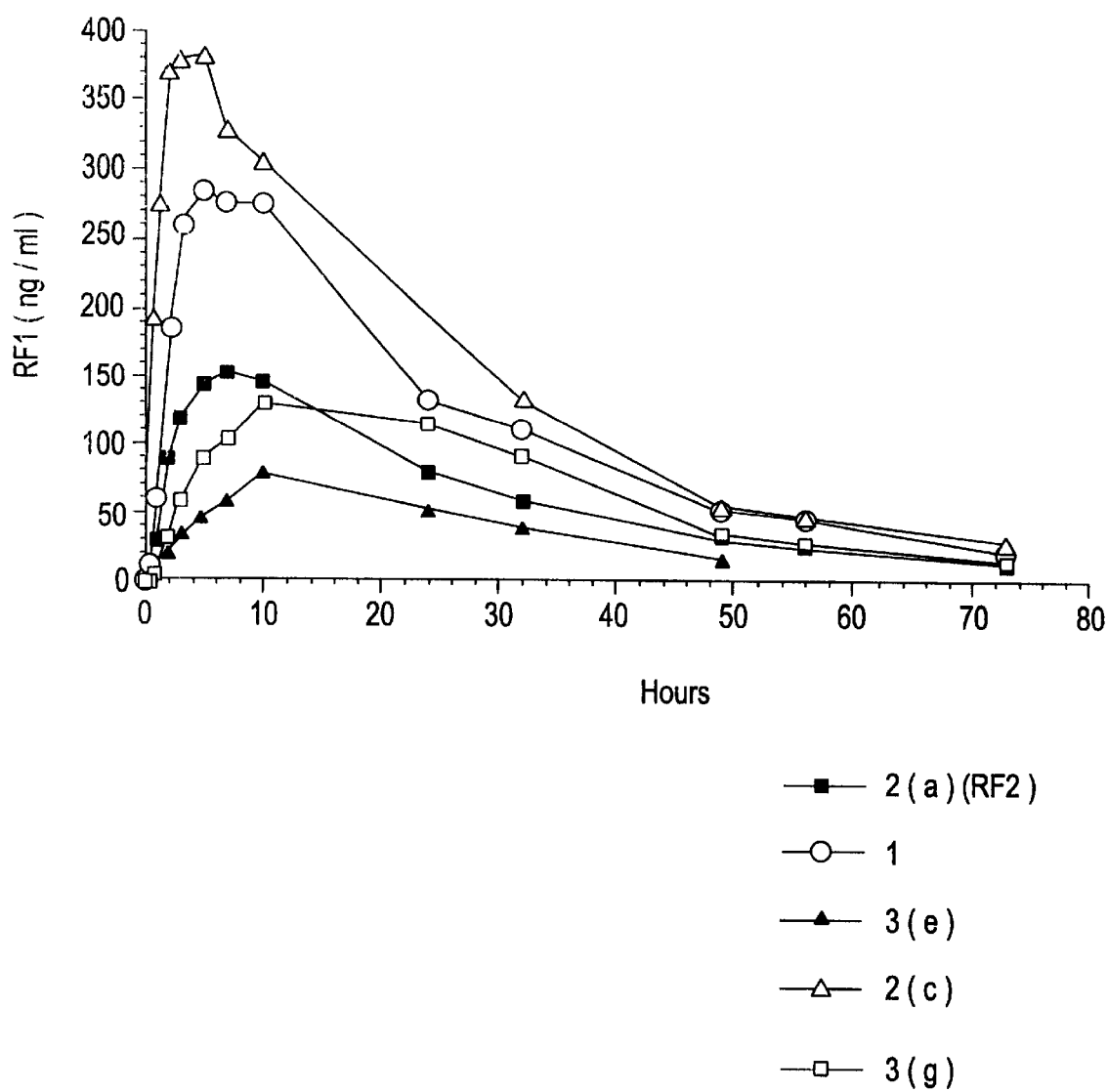

The present invention relates to compounds of the formula I and formula II or pharmaceutically acceptable salts thereof.

Preferred embodiments exemplifying the invention are the following compounds:

N-[[[(3S)-1-[4-[(hydroxyamino)iminomethyl]phenyl]-2-oxo-3-pyrrolidinyl]amino]carbonyl]-β-alanine ethyl ester monohydrochloride;

N-[[[(3S)-1-[4-[(hydroxyamino)iminomethyl]phenyl]-2-oxo-3-pyrrolidinyl]-amino]carbonyl]-β-alanine methyl ester;

N-[[[(3S)-1-[4-[(hydroxyamino)iminomethyl]phenyl]-2-oxo-3-pyrrolidinyl]-amino]carbonyl]-β-alanine 1-methyl ethyl ester monohydrochloride;

N-[[[(3S)-1-[4-[(hydroxyamino)iminomethyl]phenyl]-2-oxo-3-pyrrolidinyl]-amino]carbonyl]-β-alanine propyl ester monohydrochloride;

N-[[[(3S)-1-[4-[(hydroxyamino)iminomethyl]phenyl]-2-oxo-3-pyrrolidinyl]-amino]carbonyl]-β-alanine 2-methylpropyl ester monohydrochloride;

N-[[[(3S)-1-[4-[(hydroxyamino)iminomethyl]phenyl]-2-oxo-3-pyrrolidinyl]-amino]carbonyl]-β-alanine butyl ester monohydrochloride;

N-[[[(3S)-1-[4-[(hydroxyamino)iminomethyl]phenyl]-2-oxo-3-pyrrolidinyl]-amino]carbonyl]-β-alanine 2,2-dimethylpropyl ester;

N-[[[(3S)-1-[4-[(hydroxyamino)iminomethyl]phenyl]-2-oxo-3-pyrrolidinyl]-amino]carbonyl]-β-alanine phenylmethyl ester monohydrochloride monohydrate;

N-[[[(3S)-1-[4-[(hydroxyamino)iminomethyl]phenyl]-2-oxo-3-pyrrolidinyl]-amino]carbonyl]-β-alanine pentyl ester monohydrochloride;

N-[[[(3S)-1-[4-[(hydroxyamino)iminomethyl]phenyl]-2-oxo-3-pyrrolidinyl]-amino]carbonyl]-β-alanine 1,1-dimethylethyl ester;

N-[[[(3S)-1-[4-[imino[[[(4-methyl-1-piperazinyl)-carbonyl]oxy]amino]-methyl]phenyl]-2-oxo-3-pyrrolidinyl]amino]carbonyl]-β-alanine methyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine methyl ester monohydrochloride;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine methyl ester;

N-[[[(3S)-1-[4-(1-imino-5,9-dimethyl-4-oxo-3-oxa-2,5,9-triazadec-1-yl)-phenyl]-2-oxo-3-pyrrolidinyl]amino]carbonyl]-β-alanine methyl ester monohydrochloride;

N-[[[(3S)-1-[4-[imino[[[(4-methyl-1-piperazinyl)carbonyl]oxy]amino]-methyl]phenyl]-2-oxo-3-pyrrolidinyl]amino]carbonyl]-β-alanine ethyl ester dihydrochloride;

N-[[[(3S)-1-[4-(1-imino-5,8-dimethyl-4-oxo-3-oxa-2,5,8-triazanon-1-yl)phenyl]2-oxo-3-pyrrolidinyl]amino]carbonyl]-β-alanine ethyl ester dihydrochloride;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine ethyl ester monoacetate;

N-[[[(3S)-1-[4-(1-imino-5,9-dimethyl-4-oxo-3-oxa-2,5,9-triazadec-1-yl)phenyl]2-oxo-3-pyrrolidinyl]amino]carbonyl]-β-alanine ethyl ester dihydrochloride;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 1-methylethyl ester dihydrochloride;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine 1-methylethyl ester dihydrochloride;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine 1-methylethyl ester monoacetate;

N-[[[(3S)-1-[4-(1-imino-5,9-dimethyl-4-oxo-3-oxa-2,5,9-triazadec-1-yl)-phenyl]-2-oxo-3-pyrrolidinyl]amino]carbonyl]-β-alanine 1-methylethyl ester monohydrate;

N-[[[(3S)-1-[4-[imino[[[(4-methyl-1-piperazinyl)carbonyl]oxy]amino]-methyl]phenyl]-2-oxo-3-pyrrolidinyl]amino]carbonyl]-β-alanine propyl ester dihydrochloride;

N-[[[(3S)-1-[4-(1-imino-5,8-dimethyl-4-oxo-3-oxa-2,5,8-triazanon-1-yl)phenyl]2-oxo-3-pyrrolidinyl]amino]carbonyl]-β-alanine propyl ester dihydrochloride;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine propyl ester monoacetate monohydrate;

N-[[[(3S)-1-[4-(1-imino-5,9-dimethyl-4-oxo-3-oxa-2,5,9-triazadec-1-yl)phenyl]2-oxo-3-pyrrolidinyl]amino]carbonyl]-β-alanine propyl ester;

N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine 2-methyl propyl ester dihydrochloride;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine 2-methylpropyl ester dihydrochloride;

N-[[[(3S)-1-[4-[imino[[[(4-methyl-1-piperazinyl)carbonyl]oxy]amino]-methyl]phenyl]-2-oxo-3-pyrrolidinyl]amino]carbonyl]-β-alanine 2-methylpropyl ester dihydrochloride;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine 2-methylpropyl ester dihydrochloride;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine 2-methylpropyl ester monoacetate;

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine 2-methylpropyl ester;

N-[[[(3S)-1-[4-[imino[[[(4-methyl-1-piperazinyl)carbonyl]oxy]amino]-methyl]-phenyl]-2-oxo-3-pyrrolidinyl]amino]carbonyl]-β-alanine butyl ester dihydrochloride;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine butyl ester dihydrochloride;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine butyl ester dihydrochloride;

N-[[[(3S)-1-[4-[imino[[[(4-methyl-1-piperazinyl)carbonyl]oxy]amino]-methyl]-phenyl]-2-oxo-3-pyrrolidinyl]amino]carbonyl]-β-alanine 2,2-dimethylpropyl ester;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine 2,2-dimethylpropyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine 2,2-dimethylpropyl ester dihydrochloride, N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine phenylmethyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine phenylmethyl ester;

N-[[[(3S)-1-[4-(1-imino-8-methyl-4-oxo-3-oxa-2,5,8-triazanon-1-yl )phenyl]-2-oxo-3-pyrrolidinyl]amino]carbonyl]-β-alanine phenylmethyl ester;

N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine cyclohexyl ester dihydrochloride monohydrate;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine cyclohexyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine cyclohexyl ester monoacetate monohydrate;

N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine pentyl ester dihydrochloride;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine pentyl ester monohydrate;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine pentyl ester;

N-[[[(3S)-1-[4-[imino[[[(4-methyl-1-piperazinyl)carbonyl]oxy]amino]-methyl]phenyl]-2-oxo-3-pyrrolidinyl]amino]carbonyl]-β-alanine 1,1-dimethylethyl ester dihydrochloride;

N-[[[(3S)-1-[4-(1-imino-5,8-dimethyl-4-oxo-3-oxa-2,5,8-triazanon-1-yl)pheny]-2-oxo-3-pyrrolidinyl]amino]carbonyl]-β-alanine 1,1-dimethylethyl ester dihydrochloride;

N-[[[(3S)-1-[4-(1-imino-8-methyl-4-oxo-3-oxa-2,5,8-triazanon-1-yl)phenyl]- 2-oxo-3-pyrrolidinyl]amino]carbonyl]-β-alanine 1,1dimethylethyl ester;

N-[[[(3S)-1-[4-[[[[(dimethylamino)carbonyl]oxy]amino]imino-methyl]-phenyl]-2-oxo-3-pyrrolidinyl]amino]carbonyl]-β-alanine methyl ester;

N-[[[(3S)-1-[4-[[[[(dimethylamino)carbonyl]oxy]amino]iminomethyl]-phenyl]-2-oxo-3-pyrrolidinyl]amino]carbonyl]-β-alanine ethyl ester;

N-[[[(3S)-1-[4-[[[[(dimethylamino)carbonyl]oxy]amino]iminomethyl]phenyl]-2-oxo-3-pyrrolidinyl]amino]carbonyl]-β-alanine 1-methylethyl ester; N-[[[(3S)-1-[4-[[[[(dimethylamino)carbonyl]oxy]amino]iminomethyl]phenyl]-2-oxo-3-pyrrolidinyl]amino]carbonyl]-β-alanine propyl ester; N-[[[(3S)- 1 -[4-[[[[(dimethylamino)carbonyl]oxy]amino]iminomethyl]phenlyl]-2-oxo-3-pyrrolidinyl]amino]carbonyl]-β-alanine 2-methylpropyl ester;

N-[[[(3S)-1-[4-[[[[(dimethylamino)carbonyl]oxy]amino]iminomethyl]phenyl]-2-oxo-3-pyrrolidinyl]amino]carbonyl]-β-alanine butyl ester;

N-[[[(3S)-1-[4-[[[[(dimethylamino)carbonyl]oxy]amino]iminomethyl]phenyl]-2-oxo-3-pyrrolidinyl]amino]carbonyl]-β-alanine 2,2-methylpropyl ester;

N-[[[(3S)-1-[4-[[[[(dimethylamino)carbonyl]oxy]amino]iminomethyl]phenlyl]-2-oxo-3-pyrrolidinyl]amino]carbonyl]-β-alanine phenylmethyl ester;

N-[[[(3S)-1-[4-[[[[(dimethylamino)carbonyl]oxy]amino]iminomethyl]phenyl]-2-oxo-3-pyrrolidinyl]amino]carbonyl]-β-alanine pentyl ester;

N-[[[(3S)-1-[4-[[[[(dimethylamino)carbonyl]oxy]amino]iminomethyl]phenyl]-2-oxo-3-pyrrolidinyl]amino]carbonyl]-β-alanine 1,1-dimethylethyl ester;

N-[[[(3S)-1-[4-[[[(aminocarbonyl)oxy]amino]iminomethyl]-phenyl]-2-oxo-3-pyrrolidinyl]amino]carbonyl]-β-alanine methyl ester;

N-[[[(3S)-1-[4-[[[(aminocarbonyl)oxy]amino]iminomethyl]phenyl]-2-oxo-3-pyrrolidinyl]amino]carbonyl]-β-alanine ethyl ester;

N-[[[(3S)-1-[4-[[[(aminocarbonyl)oxy]amino]iminomethyl]phenyl]-2-oxo-3-pyrrolidinyl]amino]carbonyl]-β-alanine 1-methylethyl ester;

N-[[[(3S)-1-[4-[[[(aminocarbonyl)oxy]amino]iminomethyl]phenyl]-2-oxo-3-pyrrolidinyl]amino]carbonyl]-β-alanine propyl ester;

N-[[[(3S)-1-[4-[[[(aminocarbonyl)oxy]amino]iminomethyl]phenyl]-2-oxo-3-pyrrolidinyl]amino]carbonyl]-β-alanine 2-methylpropyl ester;

N-[[[(3S)-1-[4-[[[(aminocarbonyl)oxy]amino]iminomethyl]phenyl]-2-oxo-3-pyrrolidinyl]amino]carbonyl]-β-alanine propyl ester;

N-[[[(3S)-1-[4-[[[(aminocarbonyl)oxy]amino]iminomethyl]phenyl]-2-oxo-3-pyrrolidinyl]amino]carbonyl]-β-alanine butyl ester;

N-[[[(3S)-1-[4-[[[(aminocarbonyl)oxy]amino]iminomethyl]phenyl]-2-oxo-3-pyrrolidinyl]amino]carbonyl]-β-alanine 2,2-dimethylpropyl ester;

N-[[[(3S)-1-[4-[[[(aminocarbonyl)oxy]amino]iminomethyl]phenyl]-2-oxo-3-pyrrolidinyl]amino]carbonyl]-β-alanine phenylmethyl ester;

N-[[[(3S)-1-[4-[[[(aminocarbonyl)oxy]amino]iminomethyl]phenyl]-2-oxo-3-pyrrolidinyl]amino]carbonyl]-β-alanine cyclohexyl ester;

N-[[[(3S)-1-[4-[[[(aminocarbonyl)oxy]amino]iminomethyl]phenyl]-2-oxo-3-pyrrolidinyl]amino]carbonyl]-β-alanine pentyl ester;

N-[[[(3S)-1-[4-[[[(aminocarbonyl)oxy]amino]iminomethyl]phenyl]-2-oxo-3-pyrrolidinyl]amino]carbonyl]-β-alanine 1,1-dimethylethyl ester;

N-[[[(3S)-1-[4-[imino[[[(4-methyl-1-piperazinyl)carbonyl]oxy]-amino]methyl]-phenyl]-2-oxo-3-pyrrolidinyl]amino]carbonyl]-β-alanine mono (trifluoroacetate);

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine bis(trifluoroacetate) monohydrate;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine;

N-[[[(3S)-1-[4-[[[[(dimethylamino)carbonyl]oxy]amino]iminomethyl]phenyl]-2-oxo-3-pyrrolidinyl]amino]carbonyl]-β-alanine monohydrate;

N-[[[(3S)-1-[4-[[[(aminocarbonyl)oxy]amino]iminomethyl]phenyl]-2-oxo-3-pyrrolidinyl]amino]carbonyl]-β-alanine;

N-[[[(3S)-1-[4-[imino[(methoxycarbonyl)amino]methyl]phenyl]-2-oxo-3-pyrrolidinyl]amino]carbonyl]-β-alanine ethyl ester hydrochloride;

N-[[[(3S)-1-[4-[imino[(methoxycarbonyl)amino]methyl]phenyl]-2-oxo-3-pyrrolidinyl]amino]carbonyl]-β-alanine methyl ester;

N-[[[(3S)-1-[4-[[(acetyloxy)amino]iminomethyl]phenyl]-2-oxo-3-pyrrolidinyl]amino]carbonyl]-β-alanine ethyl ester;

N-[[[(3S)-1-[4-[[[(ethoxycarbonyl)oxy]amino]iminomethyl]phenyl]-2-oxo-3-pyrrolidinyl]amino]carbonyl]-β-alanine ethyl ester; and N-[[[(3S)-1-[4-[imino[[[(2,2,2-trichloroethoxy)carbonyl]oxy]-amino]methyl]-phenyl]-2-oxo-3-pyrrolidinyl]amino]-carbonyl]-β-alanine ethyl ester.

The invention further relates to pharmaceutical compositions containing therapeutically effective amounts of the compounds of Formula I or II and more preferably the compounds listed above.

Such compounds are double prodrugs of the pharmacologically active glycoprotein IIb/IIa antagonists, orbofiban and xemilofiban. Such compounds are designed to improve the oral bioavailability and in particular the pharmacodynamic/pharmacokinetic (PK/PD) properties of the active agents. Bioactivation of such double prodrugs to the pharmacologically active agent will occur through a combination of hepatic metabolism and plasma ester hydrolysis. The compounds of this invention are intended to influence oral bioavailability and the PK/PD properties associated with the formation and elimination of the active agent by modulating the rate of bioactivation of the double prodrug.

As used herein, the term "alkyl" refers to a straight chain or branched chain hydrocarbon radical having from 2 to 8 carbon atoms. Examples of such alkyl radicals are ethyl, n-propyl, isopropyl, n-butyl, isobutyl, sec-butyl, t-butyl, pentyl, neopentyl, hexyl, isohexyl, n-octyl and the like.

As used herein the term "alkylene" or "lower alkylene" refers to divalent linear or branched saturated hydrocarbon radicals of 1 to about 8 carbon atoms.

As used herein, the term "alkoxy" includes straight or branched chain oxy containing radicals of the formula —OR$_4$ wherein R$_4$ is an alkyl moiety as defined above. Examples of such groups are methoxy, ethoxy, n-propoxy, n-butoxy, isobutoxy, t-butoxy, sec-butoxy, isopropoxy and the like.

As used herein the terms "halo" or "halogen" refer to a chloro (Cl), fluoro (F), bromo (Br) or iodo (I) radical.

The term "aryl", as used herein denotes aromatic ring systems composed of one or more aromatic rings. Preferred aryl groups are those consisting of one, two or three benzene rings. The term "aryl" embraces aromatic radicals such as phenyl, pyridyl, naphthyl, thiophenyl, furanyl, biphenyl and the like.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The terms "arylalkyl" or "aralkyl" refer to radicals of the formula —R$^{22}$—R$^{21}$ wherein R$^{21}$ is aryl as defined above and R$^{22}$ is an alkylene as defined above. Examples of aralkyl groups include benzyl, pyridinylmethyl, phenethyl and the like.

As used herein the term "cycloalkyl" refers to saturated carbocylic ring systems containing 3 to about 8 carbon atoms. Examples of such ring systems are cyclopropyl, cyclobutyl, cyclopentyl, cyclohexyl and the like.

The term "composition" as used herein means a product which results from the mixing or combining of more than one element or ingredient.

The term "therapeutically effective amount" shall mean that amount of drug or pharmaceutical agent that will elicit the biological or medical response of a tisssue, system or animal that is being sought by a researcher or clinician.

The following is a list of abbreviations and the corresponding meanings as used interchangeably herein:

$^1$H-NMR=proton nuclear magnetic resonance
AcOH=acetic acid
Bn=benzyl
BOC=tert-butoxycarbonyl
Cat.=catalytic amount
CDI=carbonyldiimidazole
DMF=N,N-dimethylformamide
DSC=Disuccinimidoyl carbonate
Et=ethyl
EtOAc=ethyl acetate
EtOH=ethanol
g=gram(s)
GP or gp=glycoprotein
HOAc=acetic acid
HPLC=high performance liquid chromatography
i-Pr=isopropyl
L=liter
Me=methyl
MeOH=methanol
mg=milligram
ml=milliliter
mL=milliliter
m.p.=melting point
n-Bu=normal butyl
n-C$_5$H$_{11}$=normal pentyl
n-Pr=normal propyl
Pd/C=palladium on carbon
Ph=phenyl
PPP=platelet poor plasma
PRP=platelet rich plasma
RPHPLC=reverse phase high performance liquid chromatography
RF1=Reference Compound 1
RT=room temperature
TEAP=tetra-ethyl ammonium phosphate
t-Bu=tert-butyl
TFA=trifluoroacetic acid
①=heating the reaction mixture The compounds as shown in Formula I and Formula II can exist in various isomeric forms and all such isomeric forms are meant to be included. Tautomeric forms are also included as well as pharmaceutically acceptable salts of such isomers and tautomers.

In the structure and formulas herein, a bond drawn across a bond of a ring can be to any available atom on the ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J. Pharm. Sci.*, 66(1), 1–19 (1977) for additional examples of pharmaceutically acceptable salts.)

This invention also relates to a method of inhibiting platelet aggregation and more specifically, a method of treatment involving the administration of compounds of Formula I or Formula II together with pharmaceutically acceptable carriers to achieve such inhibition.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art using standard preclinical and clinical approaches in the medicinal arts.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 100 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 500 mg, preferably from about 25 to 350 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 10 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Scheme A illustrates the metabolic fate of the double prodrug and mono prodrug intermediates leading to the active agent. By either metabolic route, it has been found that the rate of amidine prodrug metabolism can be altered by the nature of the functional group attached to it. By altering the functional group, the rate of peak plasma concentration and rate of apparent elimination of the active principle can be manipulated.

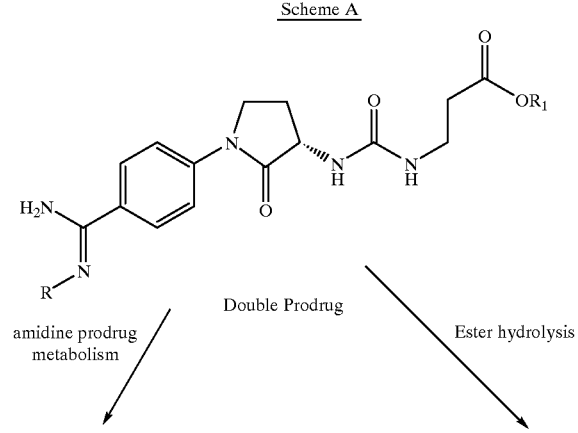

Scheme A amidine prodrug metabolism / Double Prodrug \ Ester hydrolysis

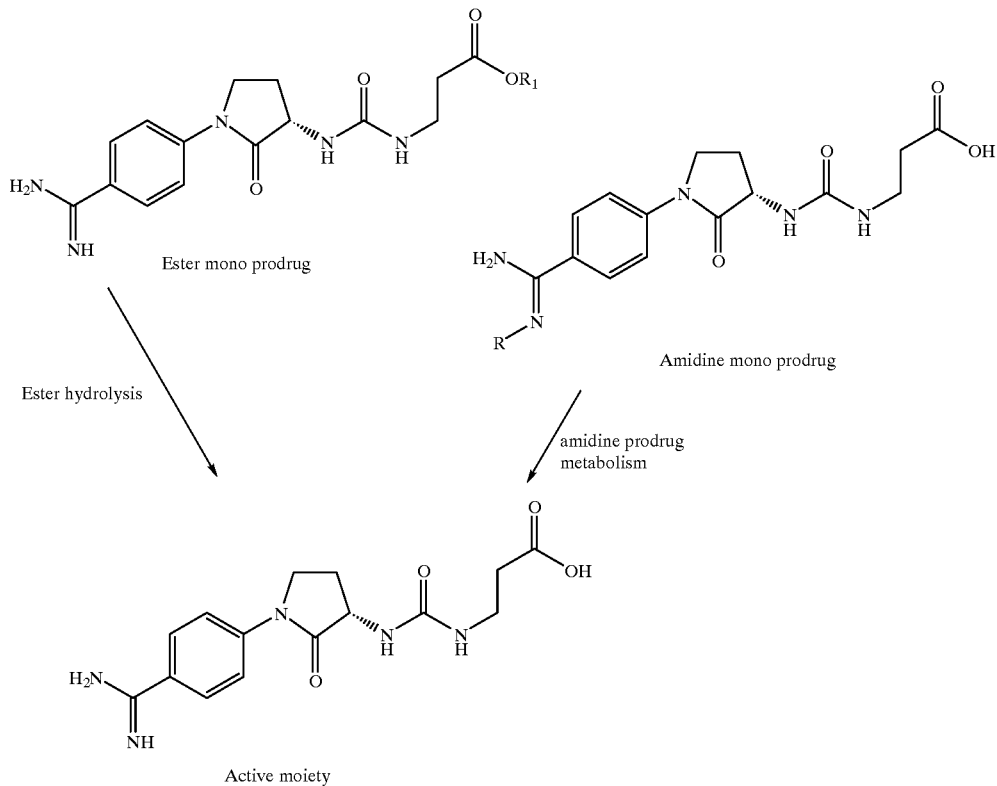

Schemes I–VI which follow are illustrative of methodology for preparing the compounds of the present invention.

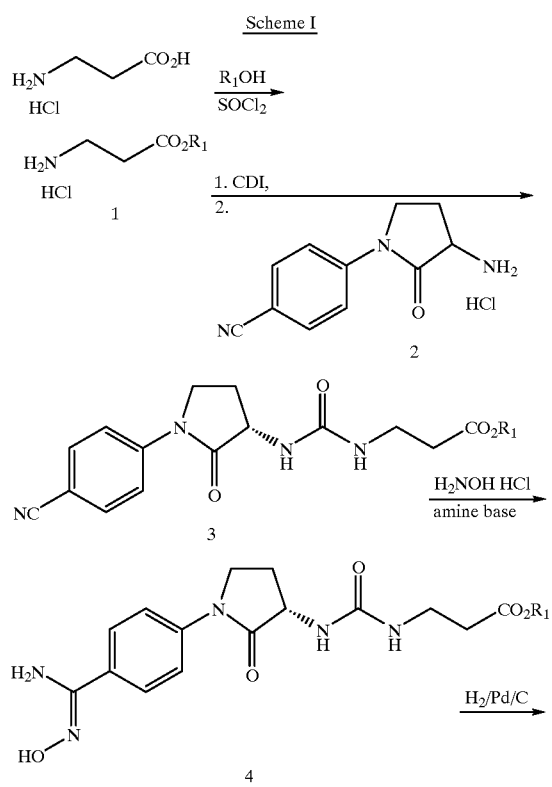

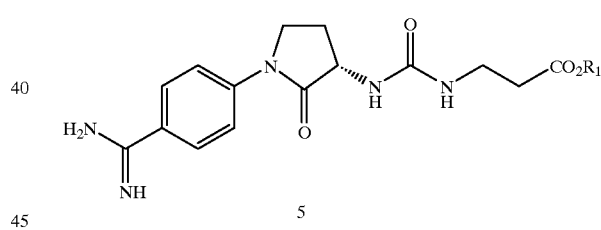

The general synthetic method for preparation of compounds of the formula I is outlined in Scheme I. In addition to commercially available beta-alanine esters, other esters are prepared by treating beta-alanine with thionyl chloride in the appropriate alcohol solvent. The corresponding ester hydrochloride 1 is coupled to the lactam 2 by the method described in U.S. Pat. No. 5,576,447, whereby the beta-alanine ester is treated with 1,1'-carbonyldiimidazole (CDI) followed by subsequent treatment with 2 in the presence of an appropriate amine base (e.g. triethylamine, diisopropylethylamine). The preparation of lactam 2 is described in U.S. Pat. No. 5,576,447. Treatment of the resulting urea, 3, with hydroxylamine hydrochloride and an appropriate amine base in an alcohol solvent afforded the amidoxime 4. Catalytic hydrogenation of 4 using a palladium catalyst affords the amidine 5.

Scheme II

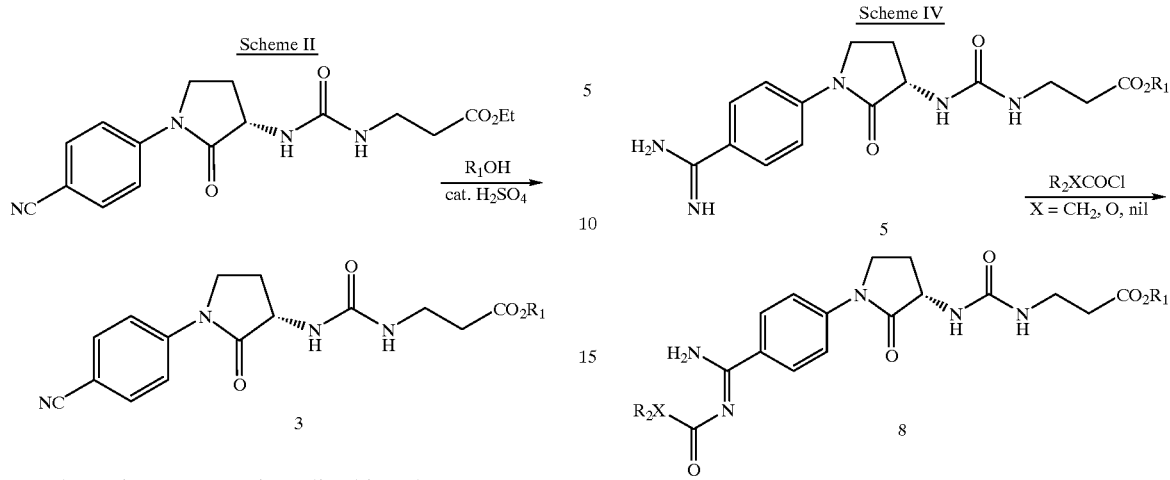

An alternative route to 3 is outlined in Scheme II. Transesterification of the ethyl ester (prepared according to the method described in U.S. Pat. No. 5,576,477) in an appropriate alcohol solvent in the presence of catalytic $H_2SO_4$ gives the corresponding ester.

Scheme IV

Both compounds 4 and 5 can be functionalized according to the methodology outlined in Schemes III and IV. Amidoxime 4 is treated with an appropriate acid chloride or chloroformate and an amine base to give the corresponding

Scheme III

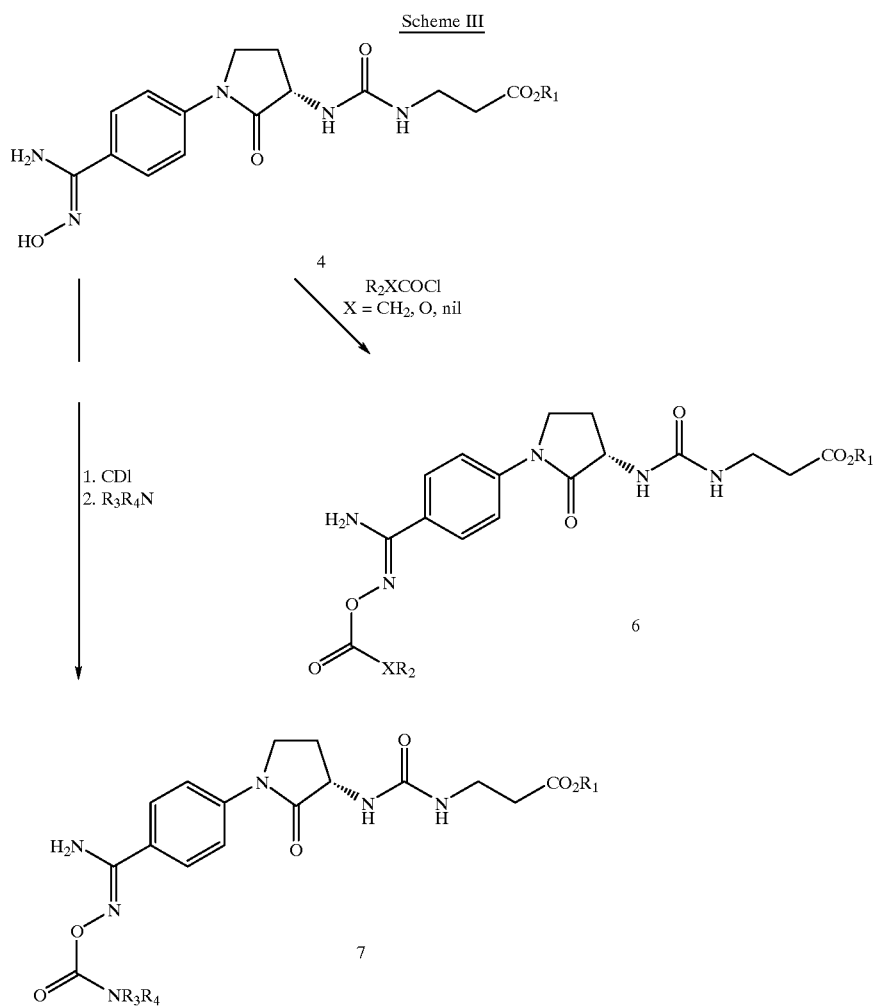

amidoxime ester or carbonate 6. Alternatively, 4 is treated with CDI followed by an appropriate primary or secondary amine to give the corresponding amidoxime carbamate 7.

The amidine 5, in a mixed aqueous/organic medium and an appropriate base (amine base or sodium bicarbonate), when treated with an acid chloride or chloroformate forms the corresponding amidine amide or amidine carbamate 8.

Scheme V

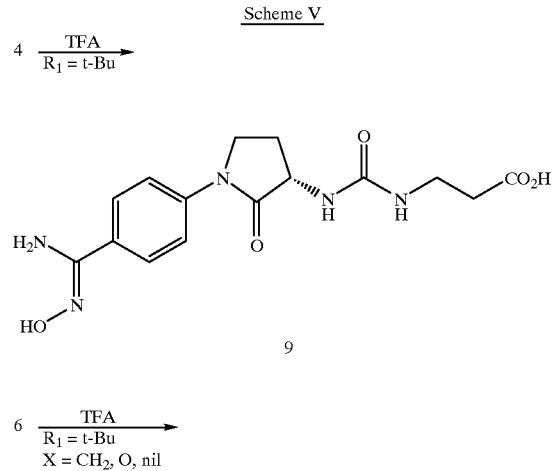

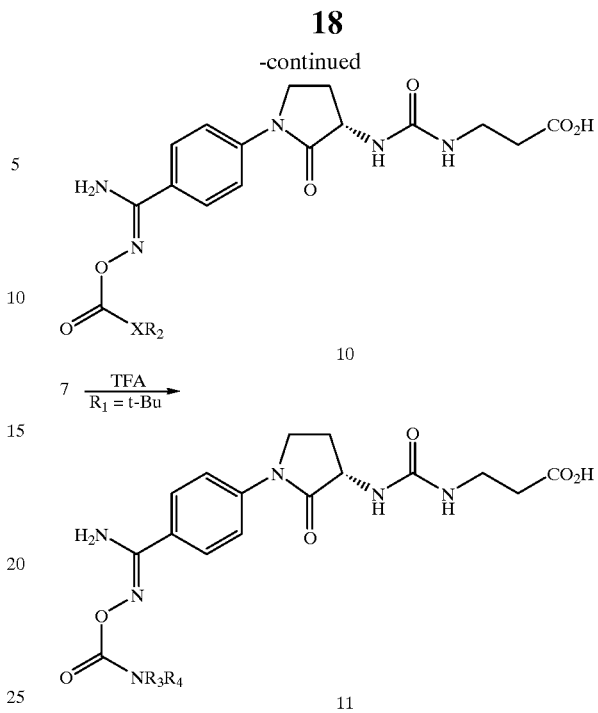

Functionalized amidine free acids are prepared according to the method outlined in Scheme V. Compound 4 ($R_1$=t-butyl) is treated with trifluoroacetic acid (TFA) to produce the free acid 9. Alternatively, compounds 6 and 7 ($R_1$=t-butyl) are treated in a similar manner to produce the corresponding free acids 10 and 11.

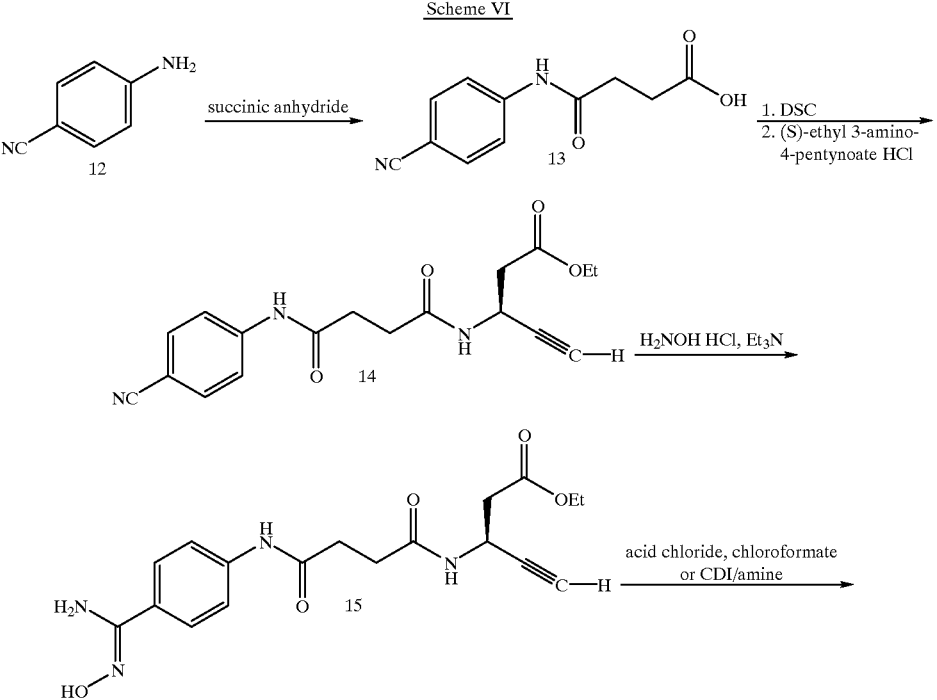

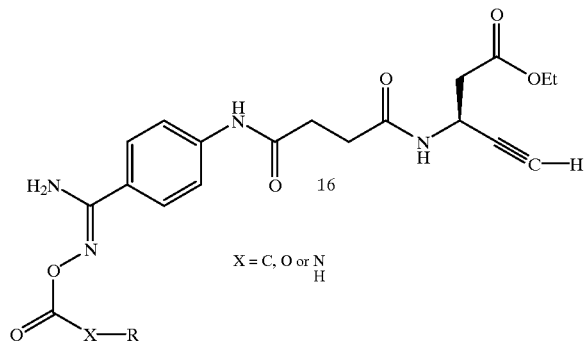

X = C, O or $\underset{H}{N}$

Xemilofiban can be prepared according to the methodology disclosed in U.S. Pat. No. 5,344,957. The direct amidine double prodrugs of xemilofiban can be prepared by methodology similar to that disclosed in Scheme IV. The synthesis of the amidoxime double prodrug and functionalized amidoxime double prodrugs can be prepared by the method outlined in Scheme VI. Condensation of 4-aminobenzonitrile 12 with succinic anhydride can afford the hemiacid 13. Activation of the acid for amide coupling with DSC can form the O-hydroxysuccinimide ester. In situ condensation of this ester with an appropriate β-alanine ester such as (S)-ethyl 3-amino-4-pentynoate HCl in the presence of a tertiary amine base can provide the nitrile ester 14. Addition of hydroxylamine to the nitrile can provide the amidoxime double prodrug 15. Further functionalization of the amidoxime with acid chlorides, chloroformates, or amines (after activation of the amidoxime with CDI) can provide a more elaborated series of double prodrugs such as 16.

The following Examples are provided to illustrate the present invention and are not intended to limit the scope thereof. Those skilled in the art will readily understand that known variations of the conditions and processes of the following preparative procedures can be used to prepare the compounds of the present invention.

EXAMPLE A

Preparation of 3-[[[[1-(4-cyanophenyl)-2-oxo-3(S)-pyrrolidinyl]amino]carbonyl]amino]propionate ethyl ester

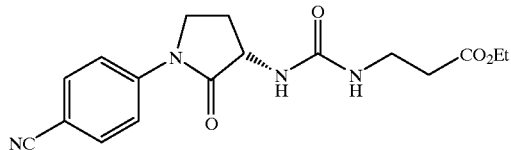

To a suspension of 1,1'-carbonyldiimidazole (572 mg, 3.55 mmol) in pyridine (2.5 mL) at 5° C. under nitrogen was added solid ethyl 3-aminopropionate hydrochloride (545 mg, 3.55 mmol). The resulting solution was stirred at 5° C. for 15 minutes, diluted with DMF (2.5 mL) and removed from the ice bath. 1-(4-Cyanophenyl)-3(S)-aminopyrrolidin-2-one hydrochloride (700 mg, 2.96 mmol) was added all at once and the reaction mixture was stirred at 75–80° C. for 2 hours. After cooling to room temperature, the resulting solution was diluted with 1 N HCl (15 mL). The white precipitate was filtered, washed with H$_2$O and dried. Trituration and filtration from methyl t-butyl ether afforded the product (844 mg) (m.p. 168.5–169° C.). Extractive work up of the filtrate with EtOAc afforded additional product (110 mg, 94% yield overall).

$[\alpha]_D^{25}$=+9.5 (MeOH, c=9.45 mg/mL) Analysis calculated. for C$_{17}$H$_{20}$N$_4$O$_4$: C, 59.29; H, 5.85; N, 16.27. Found: C, 58.94; H, 5.71; N, 16.13.

The following compounds were obtained analogously by substituting the appropriate beta alanine ester:

EXAMPLE A (a)

3-[[[[1-(4-cyanophenyl)-2-oxo-3(S)-pyrrolidinyl]amino] carbonyl]amino]propionate 1-methylethyl ester.

$^1$H-NMR (CDCl$_3$) δ 1.22 (d, J=7 Hz, 3H), 1.23 (d, J=7 Hz, 3H), 2.05, (m, 1H), 2.51 (t, J=7 Hz, 2H), 2.82 (m, 1H), 3.48 (q, J=7 Hz, 2H), 3.83 (m, 2H), 4.53 (m, 1H), 4.92 (hept, J=7 Hz, 2H), 5.52 (m, 2H), 7.67 (d, J=9 Hz, 2H), 7.81 (d, J=9 Hz, 2H).

EXAMPLE A (b)

3-[[[[1-(4-cyanophenyl)-2-oxo-3(S)-pyrrolidinyl]amino] carbonyl]amino]propionate propyl ester.

$^1$H-NMR (CDCl$_3$) δ 0.94 (t, J=7 Hz, 3H), 1.65 (m, 4H), 2.05 (m, 1H), 2.55 (t, J=7 Hz, 2H), 2.83 (m, 1H), 3.49 (q, J=7 Hz, 2H), 3.85 (m, 2H), 4.05 (t, J=7 Hz, 2H), 4.50 (m, 1H), 5.30 (d, J=7 Hz, 1H), 5.37 (t, J=7 Hz, 1H), 7.67 (d, J=9 Hz, 2H), 7.81 (d, J=9 Hz, 2H).

EXAMPLE A (c)

3-[[[[1-(4-cyanophenyl)-2-oxo-3(S)-pyrrolidinyl]amino] carbonyl]amino]propionate cyclohexyl ester.

$^1$H-NMR (CDCl$_3$) δ 1.15–1.90 (m, 10H), 2.05 (m, 1H), 2.53 (t, J=7 Hz, 2H), 2.80 (m, 1H), 3.48 (q, J=7 Hz, 2H), 3.85 (m, 2H), 4.53 (m, 1H), 4.74 (m, 1H), 5.57 (m, 2H), 7.67 (d, J=8 Hz, 2H), 7.81 (d, J=8 Hz, 2H).

EXAMPLE A (d)

3-[[[[1-(4-cyanophenyl)-2-oxo-3(S)-pyrrolidinyl]amino] carbonyl]amino]propionate 1,1-dimethylethyl ester.

$^1$H NMR (d$_6$-DMSO) δ 1.40 (s, 9H), 1.90 (m, 1H), 2.32 (t, J=7 Hz, 2H), 2.30–2.46 (m, 1H), 3.18 (br. t, J=7 Hz, 2H), 3.70–3.85 (m, 2H), 4.43 (m, 1H), 6.15 (br. s, 1H), 6.50 (br. d, J=8 Hz, 1H), 7.83 (d, J=8 Hz, 2H), 7.88 (d, J=8 Hz, 2H).

EXAMPLE A (e)

3-[[[[1-(4-cyanophenyl)-2-oxo-3(S)-pyrrolidinyl]amino] carbonyl]amino]propionate phenylmethyl ester.

$^1$H-NMR (d$_6$-DMSO) δ 1.93 (m, 1H), 2.40 (m, 1H), 2.52 (t, J=7 Hz, 2H), 3.28 (q, J=7 Hz, 2H), 3.70–3.85 (m, 2H), 4.45 (m, 1H), 5.11 (s, 2H), 6.25 (t, J=7 Hz, 1H), 6.50 (d, J=7 Hz, 1H), 7.30–7.40 (m, 5H), 7.86 (d, J=9 Hz, 2H), 7.90 (d, J=9 Hz, 2H).

EXAMPLE B

Preparation of 3-[[[[1-(4-cyanophenyl)-2-oxo-3(S)-pyrrolidinyl]amino]carbonyl]amino]propionate methyl ester

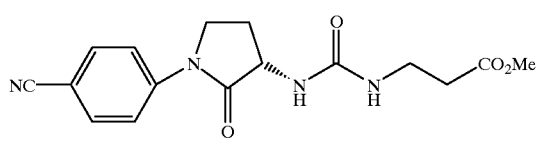

To a stirred solution of the product of Example A (10.1 g, 29.2 mmol) in MeOH (60 mL) was added concentrated sulfuric acid (0.5 mL). The reaction mixture was heated to 50° C. and stirred overnight. After cooling to room temperature, the reaction mixture was diluted with diethyl ether. The resulting precipitate was filtered, washed with EtOH:H$_2$O (9:1) and dried affording the product (9.0 g, 93% yield).

$^1$H-NMR (d$_6$-DMSO) δ 1.90 (m, 1H), 2.32–2.50 (m, 3H), 3.23 (q, J=7 Hz, 2H), 3.59 (s, 3H), 3.68–3.83 (m, 2H), 4.43 (m, 1H), 6.20 (t, J=7 Hz, 1H), 6.45 (d, J=8 Hz, 1H), 7.83 (d, J=10 Hz, 2H), 7.88 (d, J=10 Hz, 2H).

The following compounds were obtained analogously by substituting for the appropriate alcohol:

EXAMPLE B (a)

3-[[[[1-(4-cyanophenyl)-2-oxo-3(S)-pyrrolidinyl]amino]carbonyl]amino]propionate 2,2-dimethylpropyl ester. The reaction was carried out as above except THF was used as a co-solvent.

$^1$H-NMR (d$_6$-DMSO) δ 0.88 (s, 9H), 1.90 (m, 1H), 2.31–2.50 (m, 3H), 3.24 (t, 7 Hz, 2H), 3.72–3.83 (m, 4H), 4.42 (m, 1H), 6.15 (br. m, 1H), 6.42 (br. m, 1H), 7.83 (d, J=9 Hz, 2H), 7.89 (d, J=9 Hz, 2H).

EXAMPLE B (b)

3-[[[[1-(4-cyanophenyl)-2-oxo-3(S)-pyrrolidinyl]amino]carbonyl]amino]propionate 2-methylpropyl ester.

m.p. 157–158° C.; Analysis calculated. for C$_{19}$H$_{24}$N$_4$O$_4$: C, 61.28; H, 6.53; N, 15.04. Found: C, 60.98; H, 6.53; N, 14.64.

EXAMPLE B (c)

(3) 3-[[[[1-(4-cyanophenyl)-2-oxo-3(S)-pyrrolidinyl]amino]carbonyl]amino]propionate butyl ester.

$^1$H-NMR (d$_6$-DMSO) δ 0.90 (t, J=7 Hz, 3H), 1.33 (hex, J=7 Hz, 2H), 1.57 (pent, J=7 Hz, 2H), 1.93 (m, 1H), 2.35–2.50 (m, 3H), 3.25 (t, J=7 Hz, 2H), 3.70–3.85 (m, 2H), 4.03 (t, J=7 Hz, 2H), 4.46 (m, 1H), 6.21 (br. s, 1H), 6.50 (br. s, 1H), 7.86 (d, J=9 Hz, 2H), 7.91 (d, J=9 Hz, 2H).

EXAMPLE B (d)

3-[[[[1-(4-cyanophenyl)-2-oxo-3(S)-pyrrolidinyl]amino]carbonyl]amino]propionate pentyl ester.

m.p. 163–164° C. Analysis calculated. for C$_{20}$H$_{26}$N$_4$O$_4$: C, 62.16; H, 6.78; N, 14.50. Found: C, 62.02; H, 6.60; N, 14.23.

EXAMPLE 1

Preparation of N-[[[(3S)-1-[4-[(hydroxyamino)iminomethyl]phenyl]-2-oxo-3-pyrrolidinyl]amino]carbonyl]-β-alanine ethyl ester monohydrochloride

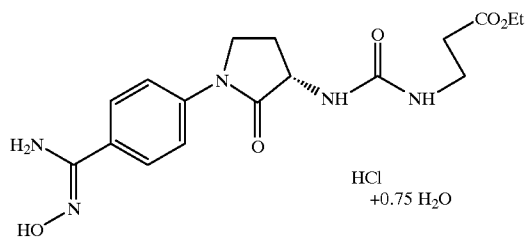

To a suspension of the product of Example A (5.7 g, 16.4 mmol) and hydroxylamine hydrochloride (5.7 g, 82.3 mmol) in EtOH (50 mL) was added triethylamine (8.3 g, 82.3 mmol). The reaction mixture was heated to 60–65° C. and stirred for 3 hours. The reaction mixture was concentrated under reduced pressure and diluted with H$_2$O. The precipitate was filtered, washed with H$_2$O and dried affording the product (5.4 g) as the free base. The product was taken up in dilute HCl and purified by RPHPLC affording the product as the hydrochloride salt as a lyophilized powder (5.4 g).

Analysis calculated. for C$_{17}$H$_{23}$N$_5$O$_5$·HCl·3/4 H$_2$O: C, 47.78; H, 6.01; N, 16.39. Found: C, 47.89; H, 6.09; N, 16.25.

The following compounds were obtained analogously:

EXAMPLE 1 (a)

N-[[[(3S)-1-[4-[(hydroxyamino)iminomethyl]phenyl]-2-oxo-3-pyrrolidinyl]amino]carbonyl]-β-alanine methyl ester m. p. 197–205° C. (dec.). Analysis calculated. for C$_{16}$H$_{21}$N$_5$O$_5$·1.3HCl: C, 46.78; H, 5.47; N, 17.05. Found: C, 46.78; H, 5.65; N, 17.21.

EXAMPLE 1 (b)

N-[[[(3S)-1-[4-[(hydroxyamino)iminomethyl]phenyl]-2-oxo-3-pyrrolidinyl]amino]carbonyl]-β-alanine 1-methylethyl ester monohydrochloride m. p. 157–162° C. (dec.). Analysis calculated. for C$_{18}$H$_{25}$N$_5$O$_5$·1.0 HCl·1.4 H$_2$O: C, 47.71; H, 6.41; N, 15.46. Found: C, 47.79; H, 6.13; N, 15.34.

EXAMPLE 1 (c)

N-[[[(3S)-1-[4-[(hydroxyamino)iminomethyl]phenyl]-2-oxo-3-pyrrolidinyl]amino]carbonyl]-β-alanine propyl ester monohydrochloride

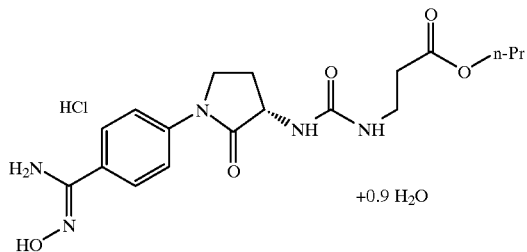

+0.9 H$_2$O m. p. 163–165° C. (dec.). Analysis calculated for C$_{19}$H$_{27}$N$_5$O$_5$·1.0 HCl·0.9 H$_2$O: C, 48.68; H, 6.31; N, 15.77. Found: C, 48.74; H, 5.99; N, 15.71.

EXAMPLE 1 (d)

N-[[[(3S)-1-[4-[(hydroxyamino)iminomethyl]phenyl]-2-oxo-3-pyrrolidinyl]amino]carbonyl]-β-alanine 2-methylpropyl ester monohydrochloride

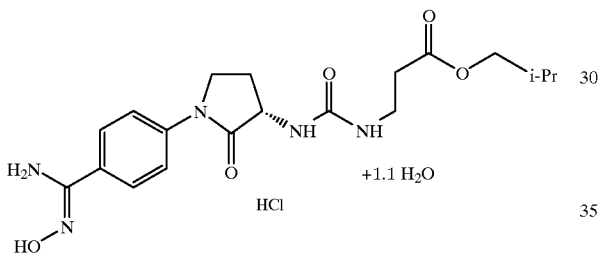

+1.1 H$_2$O $^1$H NMR (d$_6$-DMSO) δ 0.88 (d, J=8 Hz, 6H), 1.8–2.0 (m, 2H), 2.3–2.5 (m, 1H), 2.43 (t, J=7 Hz, 2H), 3.23(m, 2H), 3.76 (m, 2H), 3.81 (d, J=7 Hz, 2H), 4.43 (m, 1H), 6.22 (m, 1H), 6.51 (d, J=7 Hz, 1H), 7.75 (d, J=8 Hz, 2H), 7.89 (d, J=8 Hz, 2H), 9.0 (br s, 2H), 11.03 (s, 1H). Analysis calculated for C$_{19}$H$_{27}$N$_5$O$_5$·1.0 HCl·1.1 H$_2$O: C, 49.42; H, 6.59; N, 15.17. Found: C, 49.17; H, 6.28; N, 15.01.

EXAMPLE 1 (e)

N-[[[(3S)-1-[4-[(hydroxyamino)iminomethyl]phenyl]-2-oxo-3-pyrrolidinyl]amino]carbonyl]-β-alanine butyl ester monohydrochloride

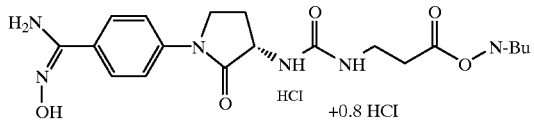

+0.8 HCl m. p. 192–193° C. (dec.). Analysis calculated for C$_{19}$H$_{27}$N$_5$O$_5$·1.0 HCl·0.8 H$_2$O: C, 50.11; H, 6.33; N, 15.21. Found: C, 50.10; H, 6.54; N, 15.35.

EXAMPLE 1 (f)

N-[[[(3S)-1-[4-[(hydroxyamino)iminomethyl]phenyl]-2-oxo-3-pyrrolidinyl]amino]carbonyl]-β-alanine 2,2-dimethylpropyl ester

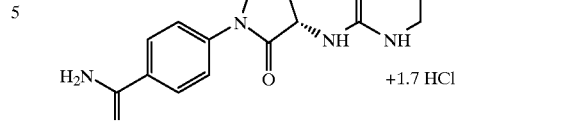

+1.7 HCl m. p. 168–170° C. (dec.). Analysis calculated for C$_{20}$H$_{29}$N$_5$O$_5$·1.7 HCl: C, 49.89; H, 6.43; N, 14.55. Found: C, 49.92; H, 6.61; N, 14.43.

EXAMPLE 1 (g)

N-[[[(3S)-1-[4-[(hydroxyamino)iminomethyl]phenyl]-2-oxo-3-pyrrolidinyl]amino]carbonyl]-β-alanine phenylmethyl ester monohydrochloride monohydrate

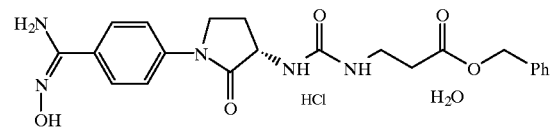

m. p. 140–145° C.; Analysis calculated for C$_{22}$H$_{25}$N$_5$O$_5$·1.0 HCl: C, 53.50; H, 5.71; N, 14.18. Found: C, 53.49; H, 5.47; N, 14.09.

EXAMPLE 1 (h)

N-[[[(3S)-1-[4-[(hydroxyamino)iminomethyl]phenyl]-2-oxo-3-pyrrolidinyl]amino]carbonyl]-β-alanine pentyl ester monohydrochloride

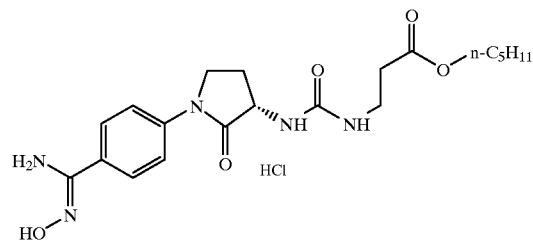

m. p. 140–145° C.; Analysis calculated for C$_{20}$H$_{29}$N$_5$O$_5$·1.0 HCl·0.8 H$_2$O: C, 51.07; H, 6.77; N, 14.89. Found: C, 51.00; H, 6.74; N, 14.64.

EXAMPLE 1 (i)

N-[[[(3S)-1-[4-[(hydroxyamino)iminomethyl]phenyl]-2-oxo-3-pyrrolidinyl]amino]carbonyl]-β-alanine 1,1-dimethylethyl ester

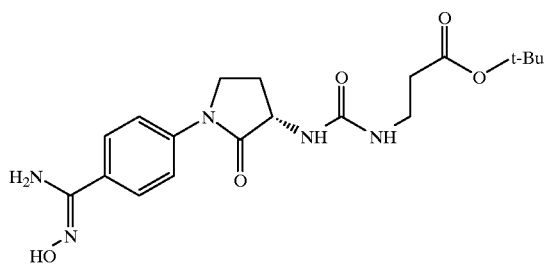

$^1$H NMR (d$_6$-DMSO) δ 1.40 (s, 9H), 1.88 (m, 1H), 2.31 (t, J=7 Hz, 2H), 2.35–2.43 (m, 1H), 3.19 (br. t, J=7 Hz, 2H), 3.70–3.83 (m, 2H), 4.40 (m, 1H), 5.32 (s, 2H), 6.12 (t, J=8 Hz, 1H), 6.47 (d, J=8 Hz, 1H), 7.67 (s, 4H), 9.58 (s, 1H).

EXAMPLE 2

Preparation of N-[[[(3S)-1-[4-(aminoiminomethyl) phenyl )-2-oxo-3-pyrrolidinyl]amino]carbonyl]-b-alanine methyl ester hydrochloride

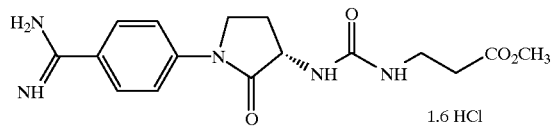

To a suspension of the product of Example 1a (773 mg, 2.1 mmol) in 50% aqueous HOAc (20 mL) was added 5% Pd/C (250 mg, 50% wet). The mixture was hydrogenated at 60° C. using 60 psi H$_2$ for 28 hours. The catalyst was filtered and the solvent evaporated under reduced pressure. The residue was taken up in dilute HCl and purified by RPHPLC affording the product (700 mg, 82% yield) as the hydrochloride salt after lyophilization [m. p. 208–216° C. (dec.)].

Analysis calculated for C$_{16}$H$_{21}$N$_5$O$_4$·1.6 HCl: C, 47.37; H, 5.61; N, 17.26. Found: C, 47.05; H, 5.97; N, 17.62.

The following compounds were prepared analogously:

EXAMPLE 2 (a) (RF2)

N-[[[(3S)-1-[4-(aminoiminomethyl)phenyl]-2-oxo-3-pyrrolidinyl]amino]carbonyl]-β-alanine ethyl ester acetate

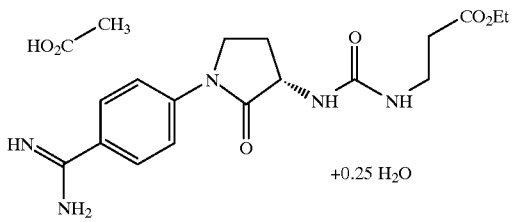

The reaction was carried out as above except HOAc was used in the RPHPLC mobile phase.

m. p. 213–214° C. (dec.) Enantiomeric purity was determined by chiral HPLC using a Chiralcel-OD column and EtOH/Heptane/TFA (20:80:0.1) as the mobile phase and was determined to be >99.9% e. e.

[Φ]$_D^{25}$=13.2 (MeOH, c=9.43 mg/mL) Analysis calculated for C$_{19}$H$_{27}$N$_5$O$_6$: C, 54.15; H, 6.46; N, 16.62. Found: C, 54.08; H, 6.57; N, 16.57.

EXAMPLE 2 (b)

N-[[[(3S)-1-[4-(aminoiminomethyl)phenyl]-2-oxo-3-pyrrolidinyl]amino]carbonyl]-β-alanine 1-methylethyl ester hydrochloride

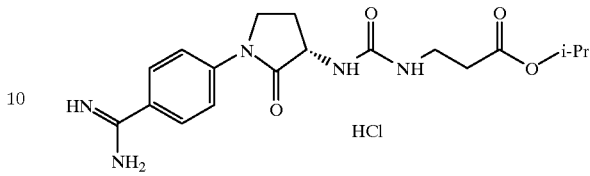

m. p. 192–193° C. (dec.). Analysis calculated for C$_{18}$H$_{25}$N$_5$O$_4$·1.5 HCl·0.5 H$_2$O: C, 49.23; H, 6.31; N, 15.95. Found: C, 49.17; H, 6.72; N, 16.09.

EXAMPLE 2 (c)

N-[[[(3S)-1-[4-(aminoiminomethyl)phenyl]-2-oxo-3-pyrrolidinyl]amino]carbonyl]-β-alanine propyl ester

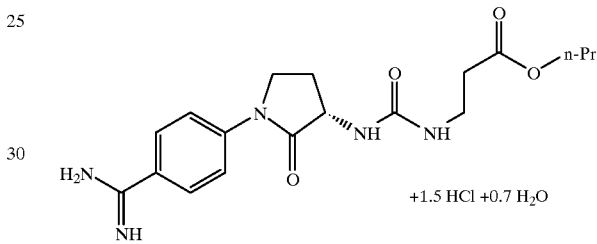

m. p. 193–204° C. (dec.). Analysis calculated for C$_{18}$H$_{25}$N$_5$O$_4$·1.5 HCl·0.7 H$_2$O: C, 48.83; H, 6.35; N, 15.82. Found: C, 48.95; H, 6.11; N, 15.74.

EXAMPLE 2 (d)

N-[[[(3S)-1-[4-(aminoiminomethyl)phenyl]-2-oxo-3-pyrrolidinyl]amino]-carbonyl]- β-alanine 2-methylpropyl ester mono(trifluoroacetate)

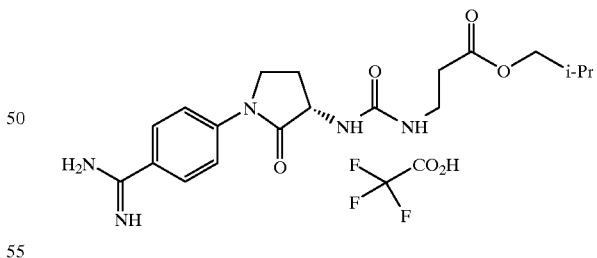

The reaction was carried out as above except TFA was used in the RPHPLC mobile phase.

m. p. 193–194° C. (dec.) Analysis calculated for C$_{19}$H$_{27}$N$_5$O$_4$·1.0 TFA: C, 50.10; H, 5.61; N, 13.91. Found: C, 49.73; H, 5.54; N, 13.80.

EXAMPLE 2 (e)

N-[[[(3S)-1-[4-(aminoiminomethyl)phenyl]-2-oxo-3-pyrrolidinyl]amino]carbonyl]-β-alanine butyl ester monohydrochloride monohydrate

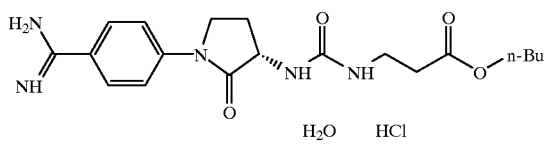

The reaction was carried out as above except HCl was used in the RPHPLC mobile phase.

m. p. 202–204° C. Analysis calculated for $C_{19}H_{27}N_5O_4 \cdot 1.0$ HCl: C, 51.41; H, 6.81; N, 15.68. Found: C, 51.21; H, 6.65; N, 15.91.

EXAMPLE 2(f)

N-[[[(3S)-1-[4-(aminoiminomethyl)phenyl]-2-oxo-3-pyrrolidinyl]amino]carbonyl]-β-alanine 2,2-dimethylpropyl ester hydrochloride

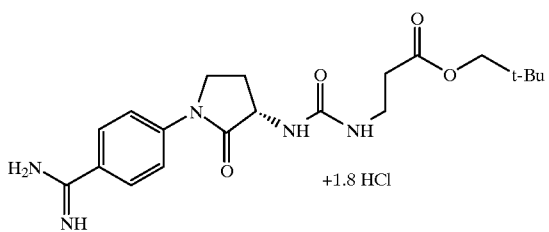

m. p. 203–205° C. (dec.). Analysis calculated for $C_{20}H_{29}N_5O_4 \cdot 1.8$ HCl: C, 51.21; H, 6.62; N, 14.93. Found: C, 51.31; H, 6.63; N, 15.27.

EXAMPLE 2(g)

N-[[[(3S)-1-[4-(aminoiminomethyl)phenyl]-2-oxo-3-pyrrolidinyl]amino]carbonyl]-β-alanine cyclohexyl ester

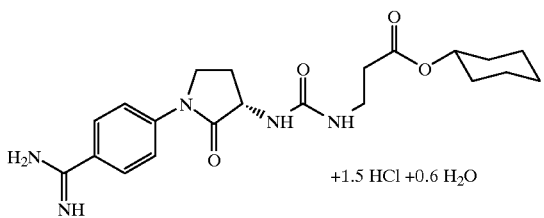

m. p. 197–199° C. (dec.). Analysis calculated for $C_{21}H_{29}N_5O_4 \cdot 1.5$ HCl 0.5 $H_2O$: C, 52.44; H, 6.64; N, 14.56. Found: C, 52.48; H, 6.45; N, 14.28.

EXAMPLE 2(h)

N-[[[(3S)-1-[4-(aminoiminomethyl)phenyl]-2-oxo-3-pyrrolidinyl]amino]carbonyl]-β-alanine pentyl ester monohydrochloride

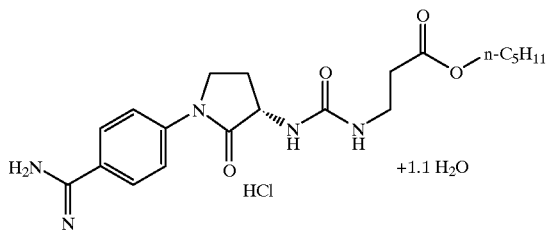

m. p. 211–212° C.; Analysis calculated for $C_{20}H_{29}N_5O_4 \cdot 1.0$ HCl·1.1 $H_2O$: C, 52.25; H, 7.06; N, 15.23. Found: C, 52.14; H, 6.85; N, 15.18.

EXAMPLE 2(i)

N-[[[(3S)-1-[4-(aminoiminomethyl)phenyl]-2-oxo-3-pyrrolidinyl]amino]carbonyl]-β-alanine 1,1-dimethylethyl ester acetate

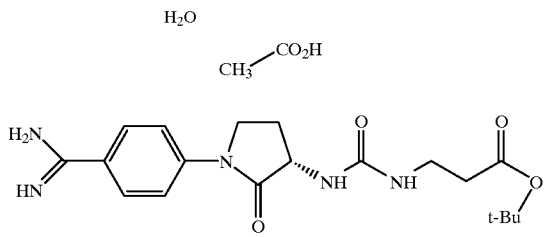

m. p. 188–189° C.; Analysis calculated for $C_{19}H_{27}N_5O_4 \cdot 1.1$ HOAc·1.0 $H_2O$: C, 53.77; H, 7.11; N, 14.79. Found: C, 53.89; H, 6.86; N, 14.45.

EXAMPLE 3

Preparation of N-[[[(3S)-1-[4-[imino[[[(4-methyl-1-piperazinyl)-carbonyl]oxy]amino]-methyl]phenyl]-2-oxo-3-pyrrolidinyl]amino]carbonyl]-β-alanine methyl ester

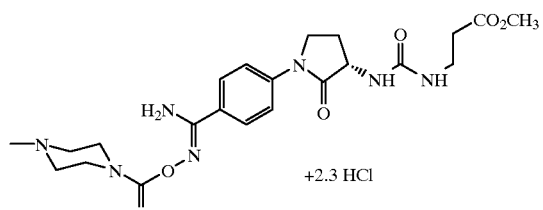

To a room temperature solution of the product of Example 1(a) (533 mg, 1.5 mmol) in DMF (4 mL) was added CDI (238 mg, 1.5 mmol). After 2 hours, to the resulting slurry was added 1-methylpiperazine (147 mg, 1.5 mmol). The resulting clear solution was stirred overnight then diluted with ether. The white solid was filtered, washed sequentially with ether, cold water ethanol, water/acetonitrile (5:95) then acetonitrile. The resulting solid was dissolved in HCl (0.4 N) and lyophilized to a dry solid affording the product (665 mg, 79% yield) [m. p. 155–157° C. (dec.)].

Analysis calculated for $C_{22}H_{31}N_7O_6 \cdot 2.3$ HCl: C, 46.08; H, 5.85; N, 17.10. Found: C, 46.03; H, 5.56; N, 16.94.

The following compounds were prepared analogously from the compounds of Example 1 and the appropriate amines:

EXAMPLE 3(a)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine methyl ester monohydrochloride

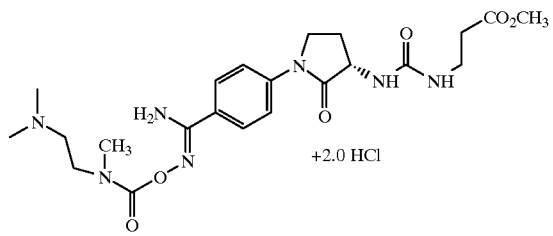

The ether precipitate was taken up in dilute HCl and purified by RPHPLC using HCl in the mobile phase.

m. p. 145–148° C. (dec.). Analysis calculated for $C_{22}H_{33}N_7O_6 \cdot 2.0$ HCl: C, 46.81; H, 6.25; N, 17.37. Found: C, 46.66; H, 6.49; N, 17.33.

EXAMPLE 3(b)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine methyl ester

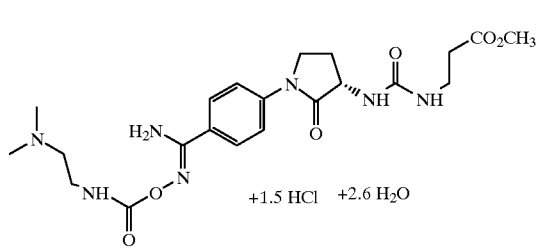

The ether precipitate was taken up in dilute HCl and purified by RPHPLC using HCl in the mobile phase.

m. p. 145–152° C. (dec.). Analysis calculated for $C_{21}H_{31}N_7O_6 \cdot 1.5$HCl 2.6 $H_2O$: C, 43.56; H, 6.56; N, 16.93. Found: C, 43.53; H, 6.34; N, 16.98.

EXAMPLE 3(c)

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine methyl ester monohydrochloride

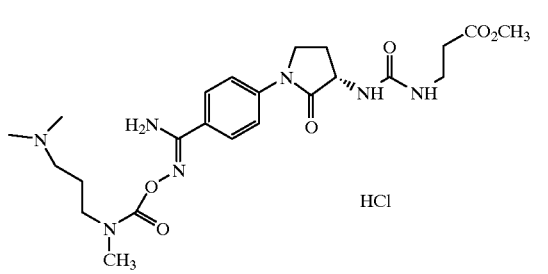

m. p. 131–136° C. Analysis calculated for $C_{23}H_{35}N_7O_6 \cdot 1.9$ HCl: C, 48.06; H, 6.47; N, 17.06. Found: C, 48.09; H, 6.53; N, 17.29.

EXAMPLE 3(d)

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine ethyl ester dihydrochloride

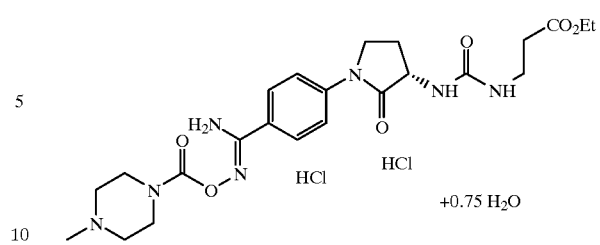

The ether precipitate was taken up in dilute HCl and purified by RPHPLC using HCl in the mobile phase.

m. p. 138–140° C. (dec.). Analysis calculated for $C_{23}H_{33}N_7O_6 \cdot 2.0$ HCl 0.75 $H_2O$: C, 46.82; H, 6.24; N, 16.62. Found: C, 46.91; H, 6.10; N, 16.68.

EXAMPLE 3(e)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine ethyl ester dihydrochloride

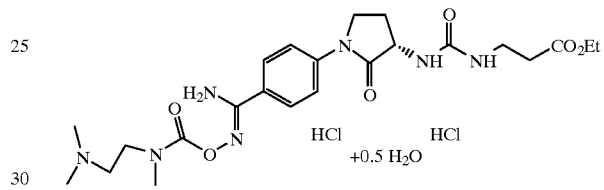

The ether precipitate was taken up in dilute HCl and purified by RPHPLC using HCl in the mobile phase.

m. p. 134–138° C. (dec). Analysis calculated for $C_{23}H_{35}N_7O_6 \cdot 2.0$ HCl·0.66 $H_2O$: C, 47.02; H, 6.52; N, 16.69. Found: C, 47.29; H, 6.87; N, 16.70.

EXAMPLE 3(f)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine ethyl ester monoacetate

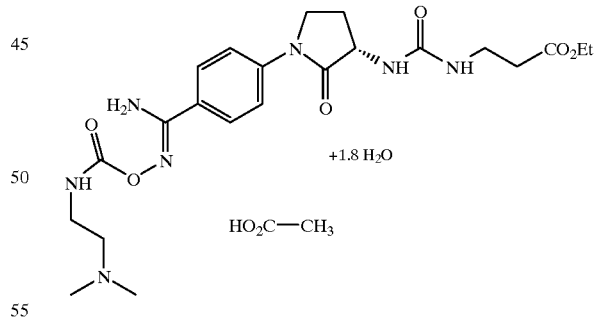

The stripped down residue was taken up in dilute aqueous HOAc and purified by RPHPLC using HOAc in the mobile phase.

m. p. 155–160° C. (dec.). Analysis calculated for $C_{22}H_{33}N_7O_6 \cdot 1.0$ HOAc·1.8 $H_2O$: C, 49.36; H, 7.01; N, 16.79. Found: C, 49.34; H, 7.12; N, 16.56.

EXAMPLE 3(g)

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine ethyl ester dihydrochloride

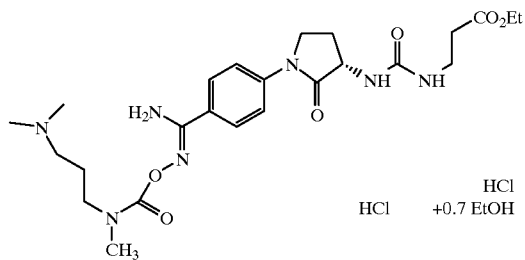

m. p. 130–133° C. Analysis calculated for $C_{24}H_{37}N_7O_6 \cdot 2.0$ HCl: C, 48.83; H, 6.97; N, 15.69. Found: C, 49.00; H, 7.03; N, 15.60.

EXAMPLE 3(h)
N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 1-methylethyl ester dihydrochloride

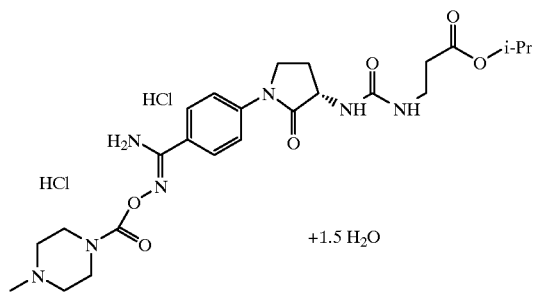

The ether precipitate was taken up in dilute HCl and purified by RPHPLC using HCl in the mobile phase.

135–136° C. (dec.). Analysis calculated for $C_{24}H_{35}N_7O_6 \cdot 2.0$ HCl·1.5 $H_2O$: C, 46.68; H, 6.53; N, 15.88. Found: C, 46.86; H, 6.44; N, 15.90.

EXAMPLE 3(i)
N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 1-methylethyl ester dihydrochloride

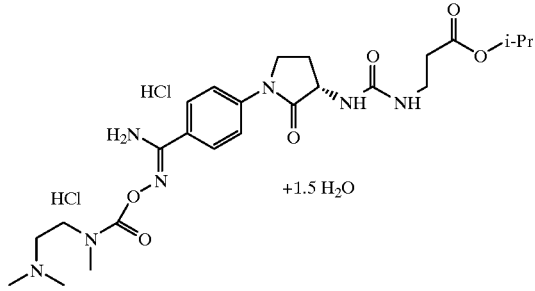

The ether precipitate was taken up in dilute HCl and purified by RPHPLC using HCl in the mobile phase.

m. p. 139–141° C. (dec.). Analysis calculated for $C_{24}H_{37}N_7O_6 \cdot 2.0$ HCl·1.5 $H_2O$: C, 46.53; H, 6.83; N, 15.83. Found: C, 46.54; H, 6.63; N, 15.78.

EXAMPLE 3(j)
N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine 1-methylethyl ester monoacetate

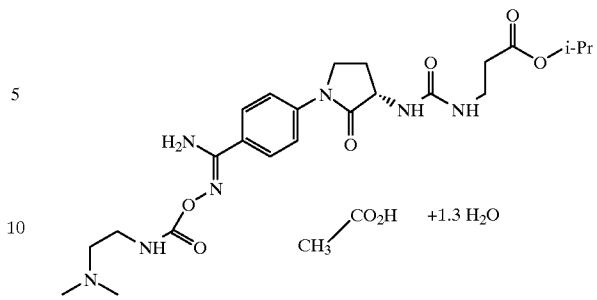

The ether precipitate was taken up in dilute HOAc and purified by RPHPLC using HOAc in the mobile phase.

m. p. 152–154° C. (dec.). Analysis calculated for $C_{23}H_{35}N_7O_6 \cdot 1.0$ HOAc·1.3 $H_2O$: C, 50.98; H, 7.12; N, 16.65. Found: C, 50.92; H, 7.03; N, 17.01.

EXAMPLE 3(k)
N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine 1-methylethyl ester monohydrate

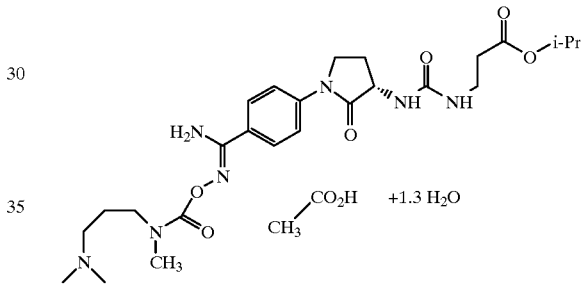

m. p. 150–152° C. (dec.). Analysis calculated for $C_{25}H_{39}N_7O_6 \cdot 2.5$ HCl·1.0 $H_2O$: C, 49.52; H, 7.06; N, 16.17. Found: C, 49.57; H, 7.33; N, 16.17.

EXAMPLE 3(l)
N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine propyl ester dihydrochloride

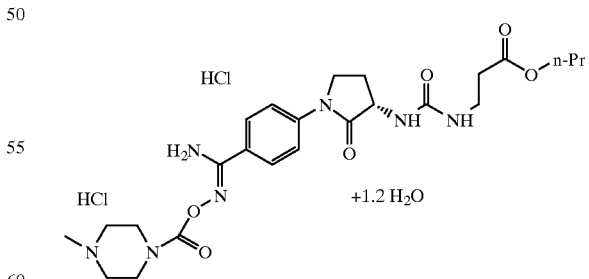

m. p. 158–160° C. (dec.).

The ether precipitate was taken up in dilute HCl and purified by RPHPLC using HCl in the mobile phase. Analysis calculated for $C_{24}H_{37}N_7O_6 \cdot 2.0$ HCl·0.5 $H_2O$: C, 48.08; H, 6.39; N, 16.35. Found: C, 48.12; H, 6.67; N, 16.24.

EXAMPLE 3(m)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine propyl ester dihydrochloride

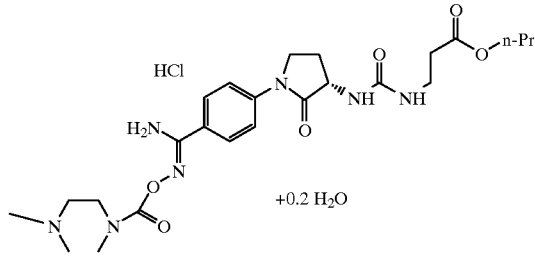

The ether precipitate was taken up in dilute HCl and purified by RPHPLC using HCl in the mobile phase.

m. p. 139–141 ° C. (dec.). Analysis calculated for $C_{24}H_{37}N_7O_6 \cdot 2.0$ HCl $0.2$ H$_2$O: C, 48.36; H, 6.66; N, 16.45. Found: C, 48.40; H, 6.74; N, 16.40.

EXAMPLE 3(n)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine propyl ester monoacetate monohydrate

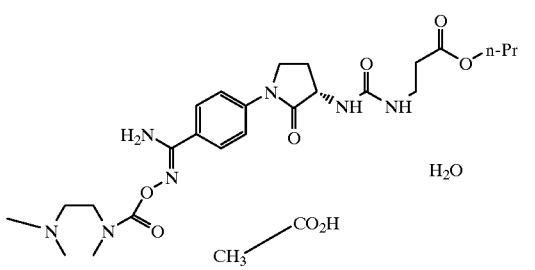

The ether precipitate was taken up in dilute HOAc and purified by RPHPLC using HOAc in the mobile phase.

m. p. 156–157° C. (dec.). Analysis calculated for $C_{23}H_{35}N_7O_6 \cdot 1.0$ HOAc $\cdot 1.0$ H$_2$O: C, 51.45; H, 7.08; N, 16.80. Found: C, 51.53; H, 7.31; N, 17.01.

EXAMPLE 3(o)

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine propyl ester

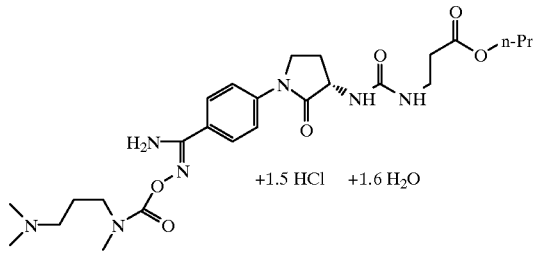

m. p. 150–152° C. (dec.). Analysis calculated for $C_{25}H_{39}N_7O_6 \cdot 1.5$ HCl $1.6$ H$_2$O: C, 48.66; H, 7.14; N, 15.89. Found: C, 48.62; H, 7.20; N, 15.79.

EXAMPLE 3(p)

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 2-methylpropyl ester dihydrochloride

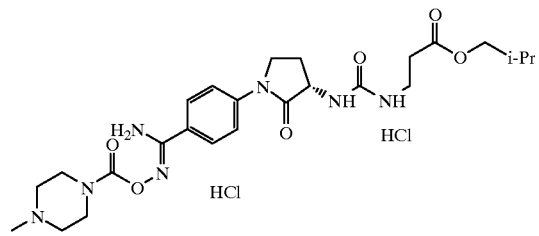

m. p. 148.5–149.5° C. (dec). Analysis calculated for $C_{25}H_{37}N_7O_6 \cdot 2.0$ HCl $\cdot 0.25$ H$_2$O: C, 48.94; H, 6.57; N, 15.98. Found: C, 48.78; H, 6.41; N, 15.99.

EXAMPLE 3(q)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 2-methylpropyl ester dihydrochloride

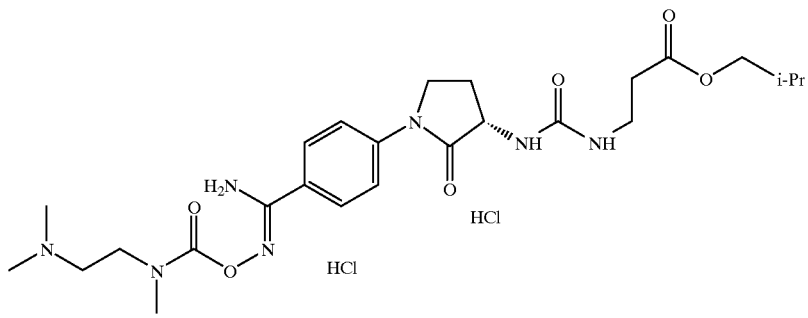

m. p. 145–146° C. (dec). Analysis calculated for $C_{25}H_{39}N_7O_6 \cdot 2.0$ HCl $\cdot 0.25$ H$_2$O: C, 49.14; H, 6.85; N, 16.05. Found: C, 48.98; H, 6.60; N, 15.99.

EXAMPLE 3(r)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine 2-methylpropyl ester monoacetate

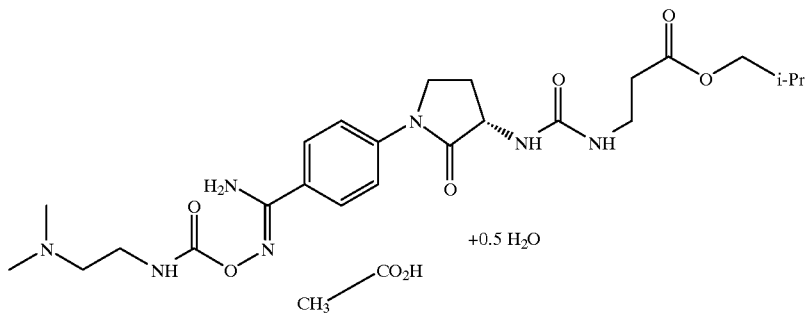

The ether precipitate was taken up in dilute HOAc and purified by RPHPLC using HOAc in the mobile phase.

m. p. 158–159° C. (dec). Analysis calculated for $C_{24}H_{37}N_7O_6 \cdot 1.0$ HOAc$\cdot 0.25$ H$_2$O: C, 53.05; H, 7.17; N, 16.66. Found: C, 53.02; H, 7.32; N, 16.78.

EXAMPLE 3(s)

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine 2-methylpropyl ester

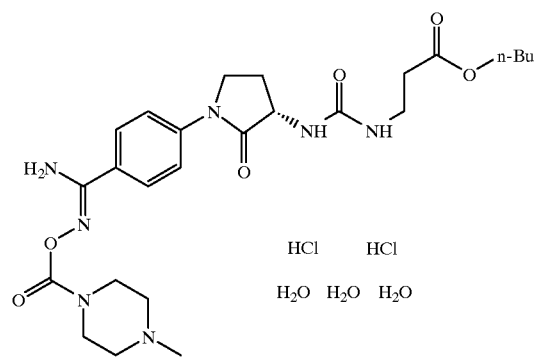

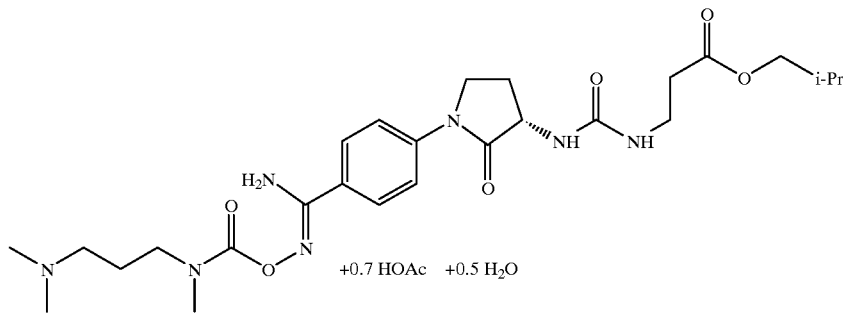

The ether precipitate was taken up in dilute HOAc and purified by RPHPLC using HOAc in the mobile phase.

m. p. 131.5–133° C; Analysis calculated for $C_{25}H_{39}N_7O_6 \cdot 0.75$ HOAc$\cdot 0.5$ H$_2$O: C, 54.89; H, 7.54; N, 16.29. Found: C, 54.57; H, 7.45; N, 16.62.

EXAMPLE 3(t)

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine butyl ester dihydrochloride m. p. 115–117° C. (dec.). Analysis calculated for $C_{25}H_{37}N_7O_6 \cdot 2.2$ HCl$\cdot 3.0$ H$_2$O: C, 45.10; H, 6.84; N, 14.72. Found: C, 45.08; H, 6.69; N, 14.75.

EXAMPLE 3(u)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine butyl ester dihydrochloride

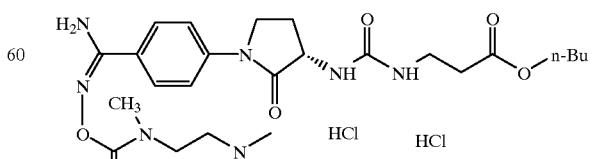

EXAMPLE 3(v)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine butyl ester dihydrochloride

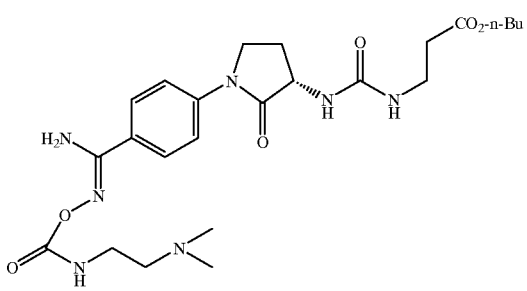

Analysis calculated for $C_{24}H_{37}N_7O_6 \cdot 2.0$ HCl·0.8 $H_2O$: C, 47.50; H, 6.74; N, 16.15. Found: C, 47.52; H, 6.56; N, 16.62.

m. p. 144–146° C. (dec.). Analysis calculated for $C_{25}H_{39}N_7O_6 \cdot 2.0$ HCl: C, 49.51; H, 6.81; N, 16.16. Found: C, 49.61; H, 7.31; N, 16.18.

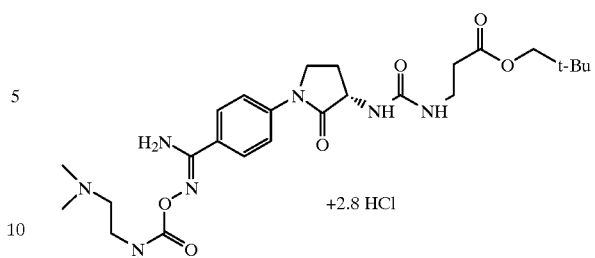

The ether precipitate was taken up in dilute HCl and purified by RPHPLC using HCl in the mobile phase.

m. p. 130–135° C. and 140° C. (dec.) Analysis calculated for $C_{26}H_{41}N_7O_6 \cdot 2.8$ HCl: C, 48.06; H, 6.79; N, 15.09. Found: C, 47.82; H, 6.69; N, 15.09.

EXAMPLE 3(v)

N-[[[(3S)-1-[4-(1-imino-8-methyl-4-oxo-3-oxa-2,5,8-triazanon-1-yl)phenyl]-oxo-3-pyrrolidinyl]amino]carbonyl]-β-alanine 2,2-dimethylpropyl ester dihydrochloride

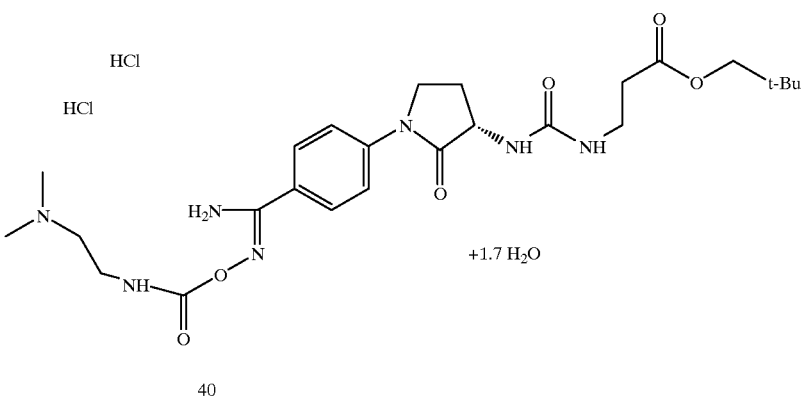

EXAMPLE 3(w)

N-[[[(3S)-1-[4-[imino[[[(4-methyl-1-piperazinyl)carbonyl]oxy]amino]methyl]phenyl]-2-oxo-3-pyrrol idinyl]amino]carbonyl]-β-alanine 2,2-dimethylpropyl ester

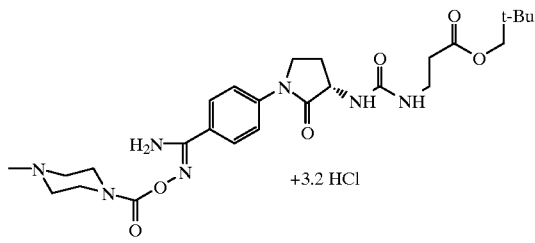

The ether precipitate was taken up in dilute HCl and purified by RPHPLC using HCl in the mobile phase.

m. p. 166–167° C. (dec.). Analysis calculated for $C_{26}H_{39}N_7O_6 \cdot 3.2$ HCl: C, 47.15; H, 6.42; N, 14.80. Found: C, 47.20; H, 6.13; N, 14.47.

EXAMPLE 3(x)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 2,2-dimethylpropyl ester The ether precipitate was taken up in dilute HCl and purified by RPHPLC using HCl in the mobile phase.

m. p. 122–126° C. and 170–190° C. (dec.) Analysis calculated for $C_{25}H_{39}N_7O_6 \cdot 2.0$ HCl·1.7 $H_2O$: C, 47.13; H, 7.02; N, 15.39. Found: C, 47.17; H, 6.63; N, 15.34.

EXAMPLE 3(z)

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine phenylmethyl ester

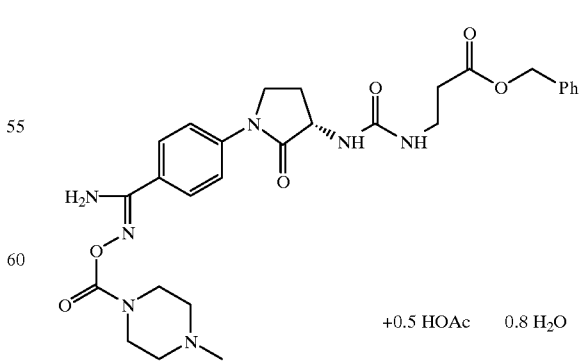

The ether precipitate was taken up in dilute HOAc and purified by RPHPLC using HOAc in the mobile phase.

m. p. 154–158° C. (dec.). Analysis calculated for $C_{28}H_{35}N_7O_6 \cdot 0.5$ HOAc·0.8 $H_2O$: C, 57.10; H, 6.38; N, 16.07. Found: C, 57.04; H, 6.08; N, 15.99.

EXAMPLE 3(aa)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine phenylmethyl ester

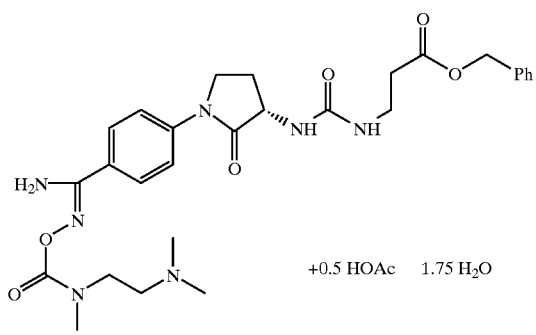

+0.5 HOAc  1.75 H₂O

The ether precipitate was taken up in dilute HOAc and purified by RPHPLC using HOAc in the mobile phase.

m. p. 68–70° C.; Analysis calculated for $C_{28}H_{37}N_7O_6 \cdot 0.5$ HOAc·1.75 $H_2O$: C, 55.34; H, 6.32; N, 16.13. Found: C, 55.44; H, 6.51; N, 15.40.

EXAMPLE 3(bb)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine phenylmethyl ester

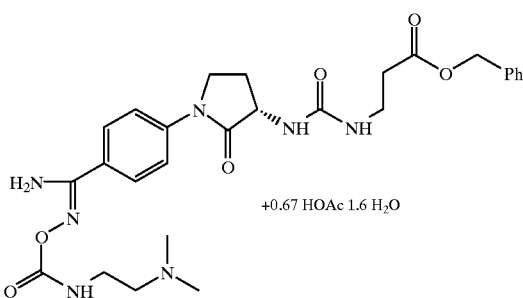

+0.67 HOAc 1.6 H₂O

The ether precipitate was taken up in dilute HOAc and purified by RPHPLC using HOAc in the mobile phase.

m. p. 159–161° C. (dec.). Analysis calculated for $C_{27}H_{35}N_7O_6 \cdot 0.67$ HOAc·1.60 $H_2O$: C, 54.68; H, 6.62; N, 15.76. Found: C, 54.44; H, 6.13; N, 15.72.

EXAMPLE 3(cc)

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine cyclohexyl ester dihydrochloride monohydrate

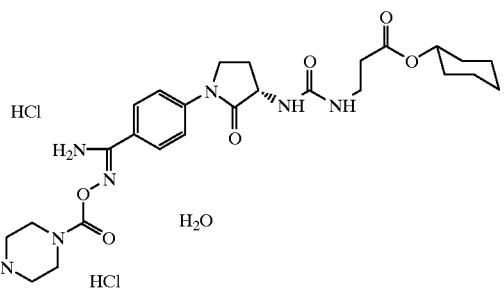

The ether precipitate was taken up in dilute HCl and purified by RPHPLC using HCl in the mobile phase.

m. p. 137–139° C. (dec.). Analysis calculated for $C_{24}H_{35}N_7O_6 \cdot 2.0$ HCl·1.2 $H_2O$: C, 47.09; H, 6.49; N, 16.02. Found: C, 47.00; H, 6.15; N, 15.99.

EXAMPLE 3(dd)

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine cyclohexyl ester

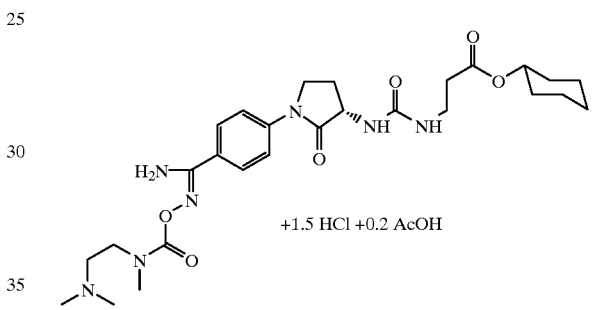

+1.5 HCl +0.2 AcOH

The ether precipitate was taken up in dilute HCl and purified by RPHPLC using HCl in the mobile phase.

m. p. 135–137° C. (dec.). Analysis calculated for $C_{27}H_{41}N_7O_6 \cdot 1.6$ HCl: C, 52.47; H, 6.95; N, 15.87. Found: C, 52.51; H, 7.08; N, 15.62.

EXAMPLE 3(ee)

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine cyclohexyl ester monoacetate monohydrate

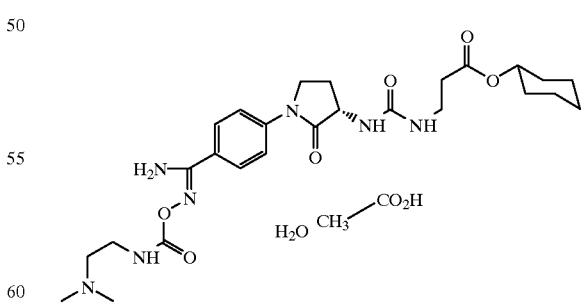

The ether precipitate was taken up in dilute HOAc and purified by RPHPLC using HOAc in the mobile phase.

m. p. 157–158° C. (dec.). Analysis calculated for $C_{26}H_{39}N_7O_6 \cdot 1.0$ HOAc·1.0 $H_2O$: C, 53.92; H, 7.27; N, 15.72. Found: C, 53.84; H, 7.13; N, 15.78.

EXAMPLE 3,(ff)
N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine pentyl ester dihydrochloride

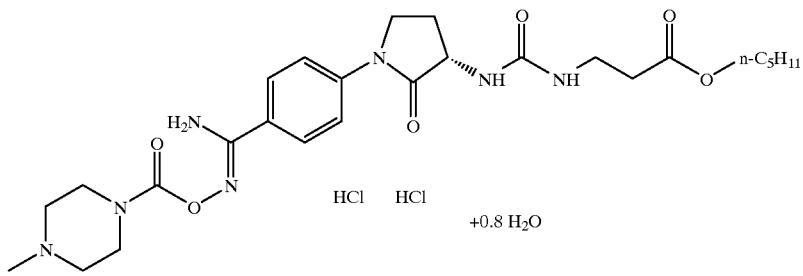

The ether precipitate was taken up in dilute HCl and purified by RPHPLC using HCl in the mobile phase.

m. p. 165–167° C. (dec.). Analysis calculated for $C_{26}H_{39}N_7O_6 \cdot 2.0$ HCl·1.0 $H_2O$: C, 49.06; H, 6.81; N, 15.40. Found: C, 49.46; H, 6.50; N, 15.34.

EXAMPLE 3 (gg)
N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine pentyl ester monohydrate

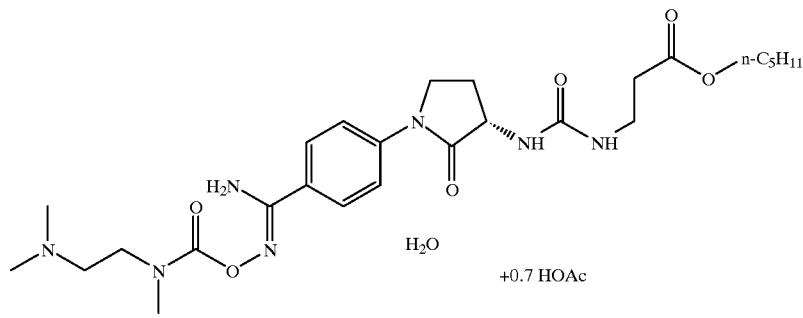

The ether precipitate was taken up in dilute HOAc and purified by RPHPLC using HOAc in the mobile phase.

m. p. 126–127° C. (dec.). Analysis calculated for $C_{26}H_{41}N_7O_6 \cdot 0.7$ HOAc·1.0 $H_2O$: C, 54.22; H, 7.60; N, 16.21. Found: C, 53.98; H, 7.46; N, 16.60.

EXAMPLE 3 (hh)
N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine pentyl ester

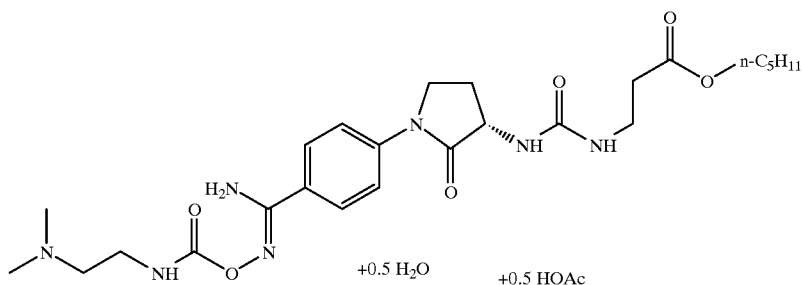

The ether precipitate was taken up in dilute HOAc and purified by RPHPLC using HOAc in the mobile phase.

m. p. 159–160° C. (dec.). Analysis calculated for $C_{25}H_{39}N_7O_6 \cdot 0.5$ HOAc·0.5 $H_2O$: C, 54.53; H, 7.39; N, 17.12. Found: C, 54.41; H, 7.25; N, 17.46.

EXAMPLE 3 (ii)
N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine 1,1-dimethylethyl ester dihydrochloride

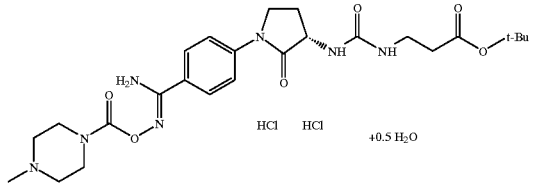

$^1$H NMR (d$_6$-DMSO) δ 1.39 (s, 9H), 1.88 (m,1H), 2.32 (t, J=7 Hz, 2H), 2.37–2.44 (m,1H), 2.75 (d, J=5 Hz, 3H), 3.01 (m, 2H), 3.18 (t, J=7 Hz, 2H), 3.23–3.41 (m, 4H), 3.70–3.80 (m, 2H), 4.41 (m, 1H) 6.16 (br. s, 1H), 6.50 (br.s, 1H), 6.77 (br.s, 2H), 7.71 (d, J=9 Hz, 2H), 7.74 (d, J=9 Hz, 2H).

EXAMPLE 3 (jj)
N-[[[(3S)-1-[4-(1-imino-5,8-dimethyl4-oxo-3-oxa-2,5,8-triazanon-1-yl)phenyl]-2-oxo-3-pyrrolidinyl]amino]carbonyl]-β-alanine 1,1-dimethylethyl ester dihydrochloride

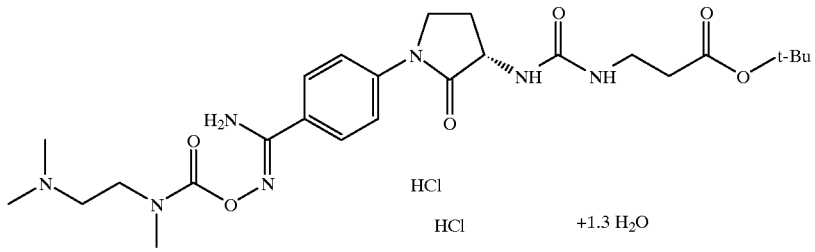

$^1$H NMR (d$_6$-DMSO) δ 1.40 (s, 9H), 1.89 (m,1H), 2.32 (t, J=7 Hz, 2H), 2.35–2.44 (m,1H), 2.79 (d, J=5 Hz, 6H), 2.96 (br. s, 3H), 3.18 (t, J=7 Hz, 2H), 3.24 (m,3H), 3.73–3.82 (m, 3H), 4.41 (m, 1H) 6.12 (br. s, 1H), 6.50 (br.s, 1H), 6.89 (br.s, 2H), 7.73 (d, J=9 Hz, 2H), 7.76 (d, J=9 Hz, 2H).

EXAMPLE 3 (kk)
N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine 1,1dimethylethyl ester

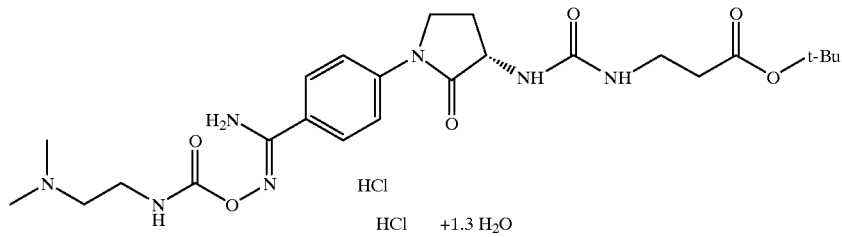

$^1$H NMR (d$_6$-DMSO) δ 1.42 (s, 9H), 2.18 (m,6H), 2.34 (t, J=7 Hz, 2H), 2.38 (t, J=7 Hz, 2H), 2.40–2.47 (m,1H), 3.20 (d, J=7 Hz, 2H), 3.25 (d, J=7 Hz, 2H), 3.74–3.82 (m, 2H), 4.38–4.48 (m, 1H), 6.14 (t, J=7 Hz, 1H), 6.48 (d, J=8 Hz, 1H), 6.77 (br.s, 2H), 7.24 (t, J=7 Hz, 2H), 7.75 (d, J=9 Hz, 2H), 7.82 (d, J=7 Hz, 2H).

EXAMPLE 4

Preparation of N-[[[(3S)-1-[4-[[[[(dimethylamino)carbonyl]oxy]amino]iminomethyl]phenyl]-2-oxo-3-pyrrolidinyl]amino]carbonyl]-β-alanine methyl ester

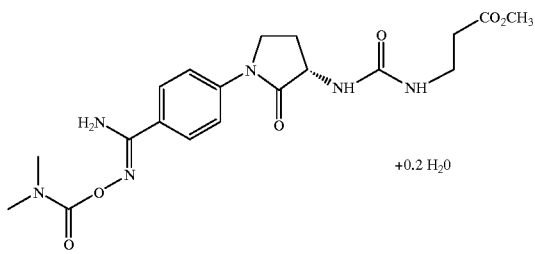

To a stirred suspension of the product of Example 1(a) (504 mg, 1.4 mmol) in pyridine (5 mL) was added dropwise dimethylcarbamoyl chloride (149 mg, 1.4 mmol). After 1 hour, the crude product was precipitated with diethyl ether, washed with water and dried affording the product (524 mg, 86% yield) [m. p. 189–192° C. (dec.)].

Analysis calculated for $C_{19}H_{26}N_6O_6 \cdot 0.2$ H$_2$O: C, 52.10; H, 6.07; N, 19.18. Found: C, 52.00; H, 6.20; N, 18.94.

The following compounds were prepared analogously:

EXAMPLE 4 (a)
N-[[[(3S)-1-[4-[[[[(dimethylamino)carbonyl]oxy]amino]iminomethyl]phenyl]-2-oxo-3-pyrrolidinyl]amino]carbonyl]-β-alanine ethyl ester carbonyl]-β-alanine 2-methylpropyl ester

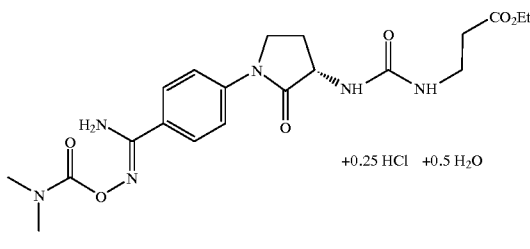

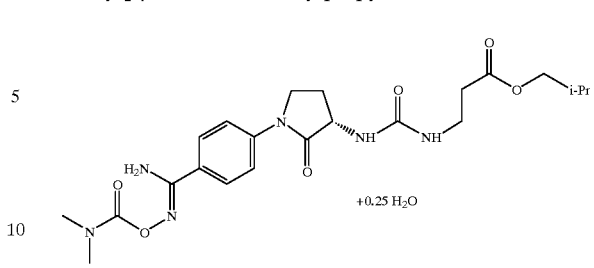

The product was purified by RPHPLC using HCl in the mobile phase.

m. p. 174° C. (dec.). Analysis calculated for $C_{20}H_{28}N_6O_6 \cdot 0.9\ H_2O$: C, 51.69; H, 6.46; N, 18.09. Found: C, 51.71; H, 6.30; N, 17.94.

The product was purified by RPHPLC using HCl in the mobile phase.

m. p. 167–168° C. (dec.). Analysis calculated for $C_{22}H_{33}N_6O_6 \cdot 0.25\ H_2O$: C, 54.93; H, 6.81; N, 17.47. Found: C, 54.71; H, 6.81; N, 17.46.

EXAMPLE 4 (b)
N-[[[(3S)-1-[4-[[[[(dimethylamino)carbonyl]oxy]amino]iminomethyl]phenyl]-2-oxo-3-pyrrolidinyl]amino]carbonyl]-β-alanine 1-methylethyl ester

EXAMPLE 4 (e)
N-[[[(3S)-1-[4-[[[[(dimethylamino)carbonyl]oxy]amino]iminomethyl]phenyl]-2-oxo-3-pyrrolidinyl]amino]carbonyl]-β-alanine butyl ester

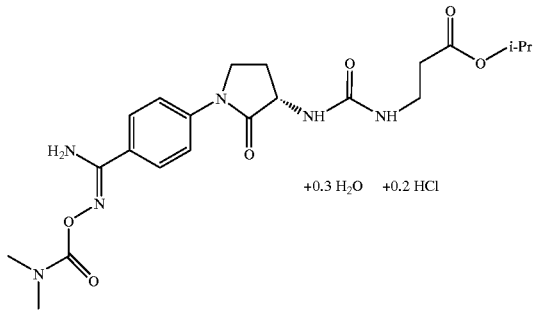

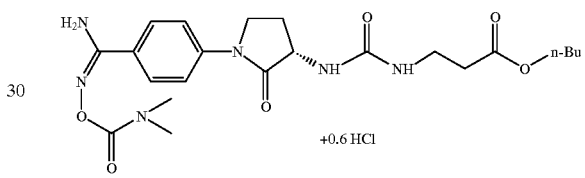

The product was purified by RPHPLC using HCl in the mobile phase.

m. p. 174–176° C. (dec.). Analysis calculated for $C_{21}H_{30}N_6O_6 \cdot 0.2\ HCl \cdot 0.3\ H_2O$: C, 53.08; H, 6.53; N, 17.69. Found: C, 52.99; H, 6.73; N, 17.63.

m. p. 176–177° C.; Analysis calculated for $C_{22}H_{32}N_6O_6 \cdot 0.6\ HCl$: C, 53.02; H, 6.59; N, 16.86. Found: C, 53.12; H, 6.58; N, 17.05.

EXAMPLE 4 (c)
N-[[[(3S)-1-[4-[[[[(dimethylamino)carbonyl]oxy]amino]iminomethyl]phenyl]-2-oxo-3-pyrrolidinyl]amino]carbonyl]-β-alanine propyl ester

EXAMPLE 4 (f)
N-[[[(3S)-1-[4-[[[[(dimethylamino)carbonyl]oxy]amino]iminomethyl]phenyl]-2-oxo-3-pyrrolidinyl]amino]carbonyl]-β-alanine 2,2-methyl propyl ester

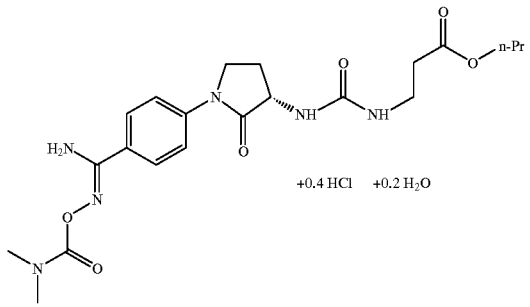

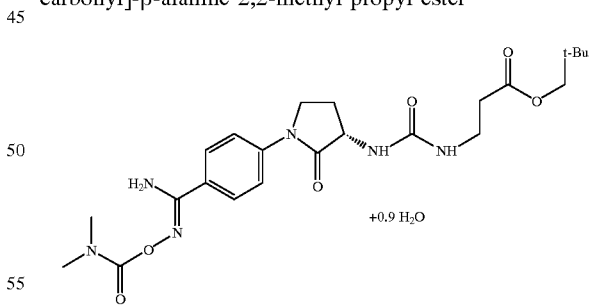

The product was purified by RPHPLC using HCl in the mobile phase.

m. p. 170–175° C. (dec.). Analysis calculated for $C_{21}H_{30}N_6O_6 \cdot 0.4\ HCl \cdot 0.2\ H_2O$: C, 52.49; H, 6.46; N, 17.48. Found: C, 52.66; H, 6.41; N, 17.34.

m. p. 177–182° C. (dec.). Analysis calculated for $C_{23}H_{34}N_6O_6 \cdot 0.9\ H_2O$: C, 54.51; H, 7.12; N, 16.58. Found: C, 54.29; H, 6.72; N, 16.37.

EXAMPLE 4 (d)
N-[[[(3S)-1-[4-[[[[(dimethylamino)carbonyl]oxy]amino]iminomethyl]phenyl]-2-oxo-3-pyrrolidinyl]amino]

EXAMPLE 4 (g)
N-[[[(3S)-1-[4-[[[[(dimethylamino)carbonyl]oxy]amino]iminomethyl]phenyl]-2-oxo-3-pyrrolidinyl]amino]carbonyl]-β-alanine phenylmethyl ester

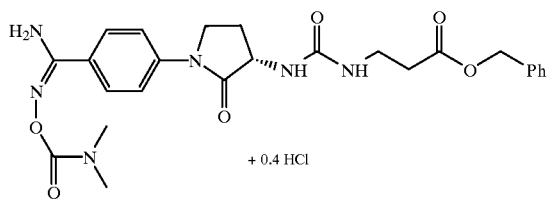

+ 0.4 HCl m. p. 179–180° C.; Analysis calculated for $C_{25}H_{30}N_6O_6 \cdot 0.8\ H_2O$: C, 57.20; H, 6.07; N, 16.01. Found: C, 57.10; H, 5.76; N, 15.66.

EXAMPLE 4 (h)

N-[[[(3S)-1-[4-[[[[(dimethylamino)carbonyl]oxy]amino]iminomethyl]phenyl]-2-oxo-3-pyrrolidinyl]amino]carbonyl]-β-alanine pentyl ester

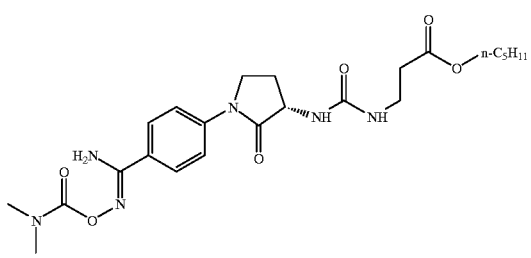

The product was purified by RPHPLC using HCl in the mobile phase.

m. p. 177–179° C. (dec.). Analysis calculated for $C_{23}H_{34}N_6O_6$: C, 56.31; H, 6.99; N, 17.13. Found: C, 56.29; H, 7.40; N, 17.03.

EXAMPLE 4 (i)

N-[[[(3S)-1-[4-[[[[(dimethylamino)carbonyl]oxy]amino]iminomethyl]phenyl]-2-oxo-3-pyrrolidinyl]amino]carbonyl]-β-alanine 1,1-dimethylethyl ester

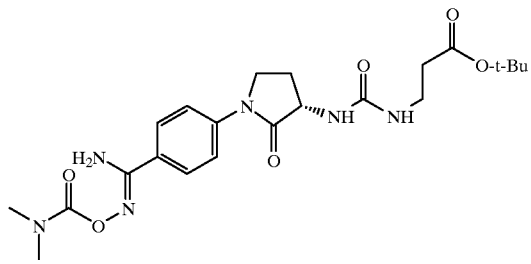

$^1$H-NMR ($d_6$-DMSO) δ 1.39 (s, 9H), 1.89 (m, 1H), 2.33 (t, J=7 Hz, 2H), 2.34 (m,1H), 2.72 (br. s, 6H), 3.19 (t, J=7 Hz, 2H), 3.70–3.82 (m, 2H), 3.38–4.48 (m, 1H), 6.15 (br. s, 1H), 6.50 (br. s, 1H), 7.28 (br. s, 2H), 7.73 (d, J=9 Hz, 2H), 7.78 (d, J=9 Hz, 2H).

EXAMPLE 5

Preparation of N-[[[(3S)-1-[4-[[[(aminocarbonyl)oxy]amino]iminomethyl]-phenyl]-2-oxo-3-pyrrolidinyl]amino]carbonyl]-β-alanine methyl ester

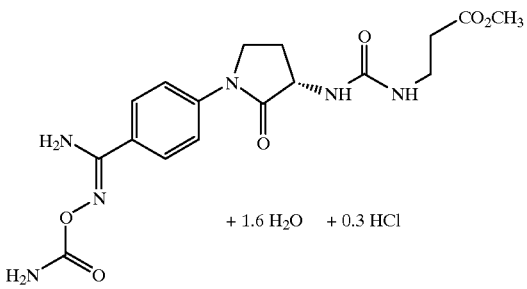

+ 1.6 H$_2$O   + 0.3 HCl

To a solution of the product of Example 1(a) (560 mg, 1.5 mmol) in water (5 mL) was added 3M HCl (0.5 mL) followed by potassium cyanate (125 mg, 1.5 mmol). After stirring for 2 hours, the precipitate was filtered. The product was redissolved in dilute HCl and purified by RPHPLC using HCl in the mobile phase affording the product as a lyophilized powder (560 mg, 75% yield) [177–178° C. (dec.)].

Analysis calculated for $C_{17}H_{22}N_6O_6 \cdot 0.3\ HCl \cdot 1.6\ H_2O$: C, 45.77; H, 5.76; N, 18.84. Found: C, 45.81; H, 5.36; N, 18.62.

The following compounds were prepared analogously:

EXAMPLE 5 (a)

N-[[[(3S)-1-[4-[[[(aminocarbonyl)oxy]amino]iminomethyl]phenyl]-2-oxo-3-pyrrolidinyl]amino]carbonyl]-β-alanine ethyl ester + 0.333 HCl   + 0.2 H$_2$O m. p. 176–177° C. (dec.). Analysis calculated for $C_{18}H_{24}N_6O_6 \cdot 0.33\ HCl \cdot 0.2\ H_2O$: C, 49.58; H, 5.72; N, 19.27. Found: C, 49.77; H, 5.73; N, 19.19.

EXAMPLE 5 (b)

N-[[[(3S)-1-[4-[[[(aminocarbonyl)oxy]amino]iminomethyl]phenyl]-2-oxo-3-pyrrolidinyl]amino]carbonyl]-β-alanine 1-methylethyl ester

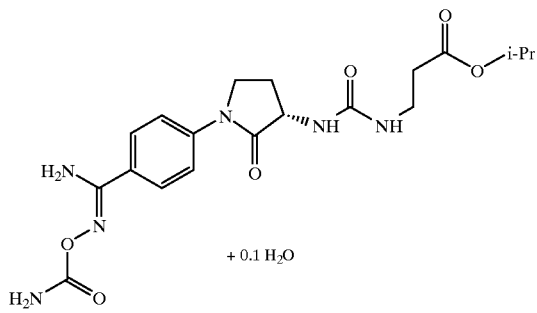

m. p. 169–172° C. (dec.). Analysis calculated for C$_{19}$H$_{26}$N$_6$O$_6$·0.1 HCl: C, 52.09; H, 6.00; N, 19.18. Found: C, 52.08; H, 6.24; N, 18.87.

EXAMPLE 5 (c)

N-[[[(3S)-1-[4-[[[(aminocarbonyl)oxy]amino]iminomethyl] phenyl]-2-oxo-3-pyrrolidinyl]amino]carbonyl]-β-alanine propyl ester

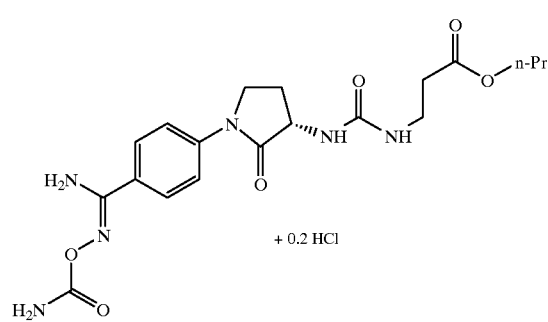

m. p. 174–176° C. (dec.). Analysis calculated for C$_{19}$H$_{26}$N$_6$O$_6$·0.2 HCl: C, 51.66; H, 5.98; N, 19.02. Found: C, 51.70; H, 5.74; N, 18.90.

EXAMPLE 5 (d)

N-[[[(3S)-1-[4-[[[(aminocarbonyl)oxy]amino]iminomethyl] phenyl]-2-oxo-3-pyrrolidinyl]amino]carbonyl]-β-alanine 2-methylpropyl ester

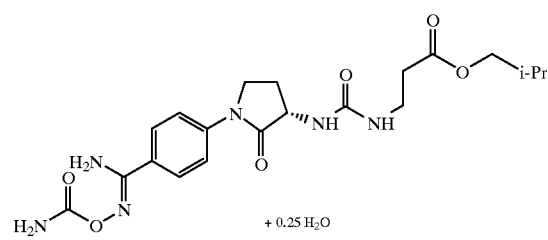

m. p. 168–169° C. (dec.). Analysis calculated for C$_{20}$H$_{28}$N$_6$O$_6$·0.25 H$_2$O: C, 53.03; H, 6.34; N, 18.55. Found: C, 53.13; H, 6.42; N, 18.61.

EXAMPLE 5 (e)

N-[[[(3S)-1-[4-[[[(aminocarbonyl)oxy]amino]iminomethyl] phenyl]-2-oxo-3-pyrrolidinyl]amino]carbonyl]-β-alanine butyl ester

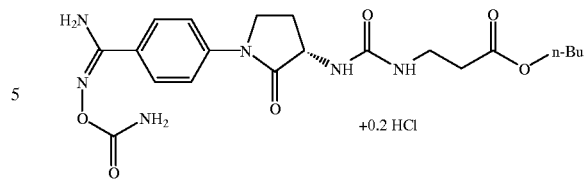

m. p. 184–186° C.; Analysis calculated for C$_{20}$H$_{28}$N$_6$O$_6$·0.2 HCl: C, 52.71; H, 6.24; N, 18.44. Found: C, 52.71; H, 6.32; N, 18.24.

EXAMPLE 5 (f)

N-[[[(3S)-1-[4-[[[(aminocarbonyl)oxy]amino]iminomethyl] phenyl]-2-oxo-3-pyrrolidinyl]amino]carbonyl]-β-alanine 2,2-dimethylpropyl ester

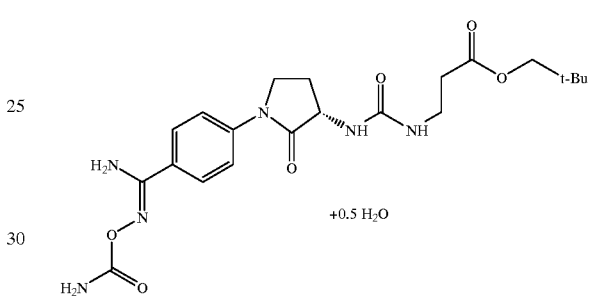

The reaction was carried out as described above except THF:water (5:1) was used as the solvent.

m. p. 169–173° C. Analysis calculated for C$_{21}$H$_{30}$N$_6$O$_6$·0.5 H$_2$O: C, 53.49; H, 6.63; N, 17.82. Found: C, 53.46; H, 6.28; N, 17.72.

EXAMPLE 5 (g)

N-[[[(3S)-1-[4-[[[(aminocarbonyl)oxy]amino]iminomethyl] phenyl]-2-oxo-3-pyrrolidinyl]amino]carbonyl]-β-alanine phenylmethyl ester

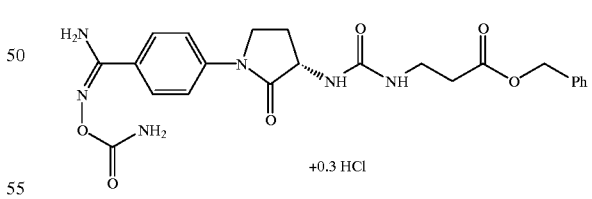

m. p. 174–176° C.; Analysis calculated for C$_{23}$H$_{26}$N$_6$O$_6$·1.0 HCl: C, 55.99; H, 5.37; N, 17.03. Found: C, 56.03; H, 5.39; N, 16.99.

EXAMPLE 5 (h)

N-[[[(3S)-1-[4-[[[(aminocarbonyl)oxy]amino]iminomethyl] phenyl]-2-oxo-3-pyrrolidinyl]amino]carbonyl]-β-alanine cyclohexyl ester

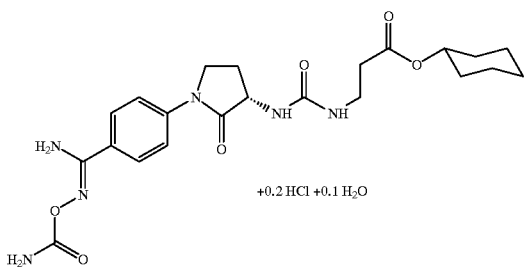

+0.2 HCl +0.1 H₂O m. p. 167–168° C. (dec.). Analysis calculated for C$_{22}$H$_{30}$N$_6$O$_6$·0.2 HCl·0.1 H$_2$O: C, 54.64; H, 6.34; N, 17.38. Found: C, 54.67; H, 6.06; N, 17.20.

EXAMPLE 5 (i)

N-[[[(3S)-1-[4-[[[(aminocarbonyl)oxy]amino]iminomethyl] phenyl]-2-oxo-3-pyrrolidinyl]amino]carbonyl]-β-alanine pentyl ester

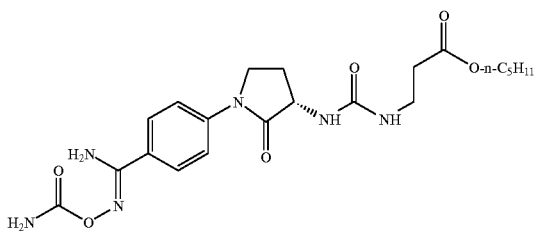

m. p. 170.5–172° C. (dec.). Analysis calculated for C$_{21}$H$_{30}$N$_6$O$_6$: C, 54.01; H, 6.58; N, 18.00. Found: C, 54.19; H, 6.45; N, 18.01.

EXAMPLE 5 (i)

N-[[[(3S)-1-[4-[[[(aminocarbonyl)oxy]amino]iminomethyl] phenyl]-2-oxo-3-pyrrolidinyl]amino]carbonyl]-β-alanine 1,1-dimethylethyl ester

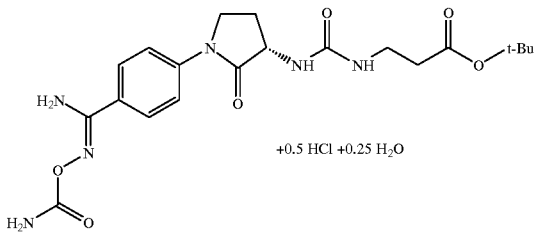

+0.5 HCl +0.25 H₂O $^1$H-NMR (d6-DMSO) δ 1.39 (s, 9H), 1.88 (m, 1H), 2.33 (t, J=7 Hz, 2H), 2.34–2.46 (m,1H), 3.19 (q, J=7 Hz, 2H), 3.72–3.80 (m, 2H), 4.40 (m, 1H), 6.13(t, J=7Hz, 1H), 6.46 (d, J=m7 Hz, 1H), 6.67 (br. s, 2H), 6.85 (br. s, 2H), 7.73 (d, J=9 Hz, 2H), 7.82 (d, J=9Hz, 2H).

EXAMPLE 6

Preparation of N-[[[(3S)-1-[4-[imino[[[(4-methyl-1-piperazinyl)carbonyl]oxy]-amino]methyl]phenyl]-2-oxo-3-pyrrolidinyl]amino]carbonyl]-β-alanine mono (trifluoroacetate)

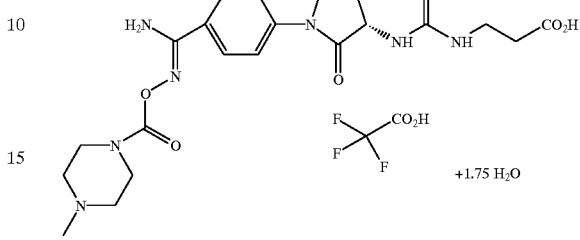

+1.75 H₂O

The product of Example 3 (ii) (660 mg, 1.24 mmol) was dissolved in trifluoroacetic acid:water (10 mL) (9:1). After stirring for 2 hours, the reaction mixture was concentrated and the residue purified on RPHPLC using TFA in the mobile phase affording the product as a lyophilized powder (308 mg, 55% yield) [m. p. 110–114° C. (dec.)].

Analysis calculated for C$_{21}$H$_{29}$N$_7$O$_6$·1.0 TFA·1.75 H$_2$O: C, 44.48; H, 5.44; N, 15.79. Found: C, 44.20; H, 5.22; N, 15.82.

The following compounds were prepared analogously from the products of Examples 3(jj), 3(kk), 4(i) and 5(j) respectively:

EXAMPLE 6 (a)

N-[[[(3S)-1-[4-(1-imino-5,8-dimethyl-4-oxo-3-oxa-2,5,8-triazanon-1-yl)phenyl]-2-oxo-3-pyrrolidinyl]amino] carbonyl]-β-alanine bis(trifluoroacetate) monohydrate

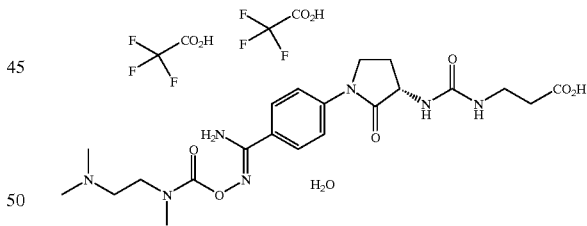

$^1$H-NMR (d$_6$-DMSO) δ 1.89 (m, 1H), 2.35 (t, J=7 Hz, 2H), 2.37–2.46 (m, 1H), 2.83 (d, J=5Hz, 6H), 2.95 (br. s, 3H), 3.20 (br. t, J=7 Hz, 2H), 3.26 (d, J=6 Hz, 2H), 3.55–3.60 (m, 2H), 3.61–3.70 (m,2H), 4.41 (br. t, J=7Hz, 1H), 6.17 (br. s, 1H), 6.47 (d, J=8Hz, 1H), 6.63 (s, 2H), 7.73 (d, J=8 Hz, 2H), 7.75 (d, J=8 Hz, 2H), 9.42 (br.s, 1H). Analysis calculated for C$_{21}$H$_{31}$N$_7$O$_6$·2.0 TFA·1.0 H$_2$O: C, 41.50; H, 4.88; N, 13.55. Found: C, 41.46; H, 4.58; N, 13.68.

EXAMPLE 6 (b)

N-[[[(3S)-1-[4-(1-imino-8-methyl-4-oxo-3-oxa-2,5,8-triazanon-1-yl )phenyl]-2-oxo-3-pyrrolidinyl]amino] carbonyl]-β-alanine

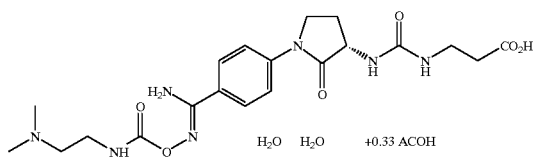

The product was repurified by RPHPLC using HOAc in the mobile phase.

m. p. 149–154° C. (dec.). Analysis calculated for $C_{20}H_{29}N_7O_6 \cdot 0.33$ HOAc·2.0 $H_2O$: C, 47.78; H, 6.66; N, 18.87. Found: C, 47.83; H, 6.55; N, 18.82.

EXAMPLE 6 (c)

N-[[[(3S)-1-[4-[[[[(dimethylamino)carbonyl]oxy]amino]iminomethyl]phenyl]-2-oxo-3-pyrrolidinyl]amino]carbonyl]-β-alanine monohydrate

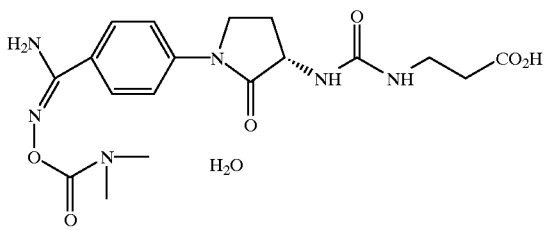

m. p. 175–178° C.; Analysis calculated for $C_{18}H_{24}N_6O_6 \cdot 1.0$ $H_2O$: C, 49.31; H, 4.98; N, 19.17. Found: C, 49.22; H, 6.10; N, 19.15.

EXAMPLE 6 (d)

N-[[[(3S)-1-[4-[[[(aminocarbonyl)oxy]amino]iminomethyl]phenyl]-2-oxo-3-pyrrolidinyl]amino]carbonyl]-β-alanine

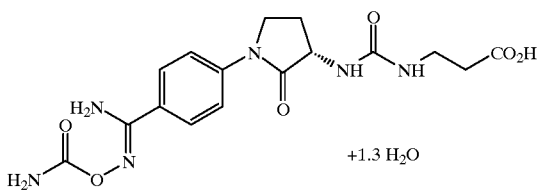

m. p. 135–140° C. (dec.). Analysis calculated for $C_{16}H_{20}N_6O_6 \cdot 1.3$ $H_2O$: C, 46.22; H, 5.48; N, 20.21. Found: C, 46.27; H, 5.30; N, 20.08.

EXAMPLE 6 (e)

N-[[[(3S)-1-[4-(Aminoiminomethyl)phenyl]-2-oxo-3-pyrrolidinyl]amino]-carbonyl]-β-alanine trifluoroacetate. Reference compound 1 (RF1)

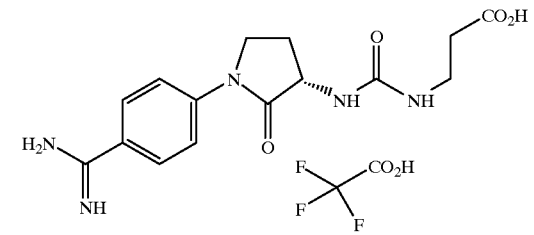

m. p. 222–223° C. (dec.). Analysis calculated for $C_{15}H_{19}N_5O_4 \cdot 1.0$ TFA·1.0 $H_2O$: C, 45.64; H, 4.51; N, 15.66. Found: C, 45.51; H, 4.36; N, 15.78.

EXAMPLE 7

N-[[[3(S)-1-[4-[imino[(phenylcarbonyl)amino]methyl]phenyl]-2-oxo-3-pyrrolidinyl]amino]carbonyl]-β-alanine ethyl ester

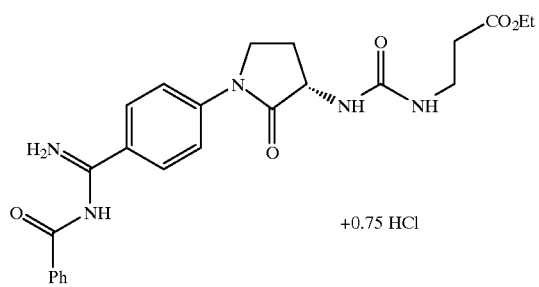

To a room temperature, stirred solution of the product of Example 2(a) (2.50 g, 5.97 mmol) and sodium bicarbonate (2.00 g, 23.7 mmol) in acetonitrile/water (20 mL) (1:1) was added benzoyl chloride (2.50 g, 17.8 mmol). After 2 hours of vigorous stirring, the reaction mixture was diluted with water and diethyl ether. The resulting biphasic suspension was filtered, washed with water then ether and dried. Recrystallization from EtOH afforded the product (800 mg) as the free base. The compound was converted to the HCl salt by suspending the solid in water (10 mL) and adding 2N HCl (1 mL). The resulting solution was lyophilized to give the product (860 mg) (m. p. 210–211° C.).

Analysis calculated for $C_{24}H_{27}N_5O_5 \cdot 1.75$ HCl: C, 54.46; H, 5.47; N, 13.23. Found: C, 54.48; H, 5.25; N, 13.23.

The following compound was prepared analogously:

EXAMPLE 7 (a)

N-[[[(3S)-1-[4-[Imino[(methoxycarbonyl)amino]methyl]phenyl]-2-oxo-3-pyrrolidinyl]amino]carbonyl]-β-alanine methyl ester

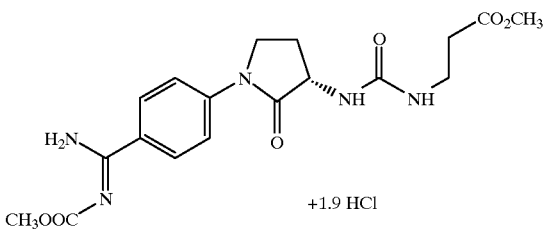

m. p. 165–166° C. (dec.). Analysis calculated for $C_{18}H_{23}N_5O_6 \cdot 1.9$ HCl: C, 45.55; H, 5.29; N, 14.75. Found: C, 45.59; H, 5.09; N, 14.89.

EXAMPLE 8

Preparation of N-[[[(3S)-1-[4-[[(acetyloxy)amino]iminomethyl]phenyl]-2-oxo-3-pyrrolidinyl]amino]carbonyl]-β-alanine ethyl ester

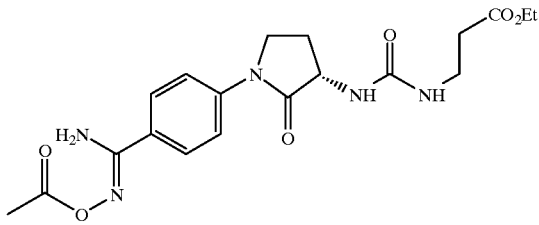

To a room temperature, stirred solution of the product of Example 1 (1.00 g, 2.65 mmol) in pyridine (6 mL) was added slowly acetic anhydride (0.27 g, 2.65 mmol). After 30 minutes of stirring the thick reaction mixture was diluted with water (25 mL) and the pyridine neutralized to pH 6–7 with concentrated HCl (~6 mL). After stirring an additional hour, the white precipitate was filtered, washed with water and dried affording the product (810 mg, 73% yield) [m. p. 188–189° C. (dec.)].

Analysis calculated for $C_{19}H_{25}N_5O_6$: C, 54.41; H, 6.01; N, 16.70. Found: C, 54.16; H, 5.77; N, 16.75.

EXAMPLE 9

Preparation of N-[[[(3S)-1-[4-[[[(ethoxycarbonyl)oxy]amino]iminomethyl]phenyl]-2-oxo-3-pyrrolidinyl]amino]carbonyl]-β-alanine ethyl ester

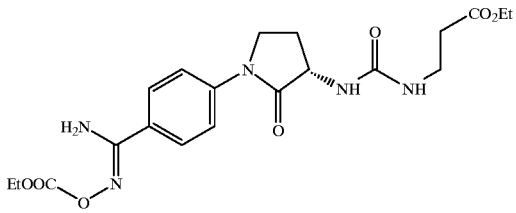

To a room temperature, stirred solution of the product of Example 1 (1.05 g, 2.78 mmol) in pyridine (6 mL) was added slowly ethyl chloroformate (0.30 g, 2.78 mmol). After 15 minutes of stirring the clear solution was diluted with water (40 mL) and the pH adjusted to 3 with concentrated HCl (~5.5 mL). The white precipitate was filtered, washed with water and dried affording the product (1.00 g, 80% yield) (m. p. 198–201° C).

Analysis calculated for $C_{20}H_{27}N_5O_7$: C, 53.45; H, 6.06; N, 15.57. Found: C, 53.36; H, 6.37; N, 15.55.

EXAMPLE 10

Preparation of N-[[[(3S)-1-[4-[imino[[[(2,2,2-trichloroethoxy)carbonyl]oxy]amino]methyl]phenyl]-2-oxo-3-pyrrolidinyl]amino]carbonyl]-β-alanine ethyl ester

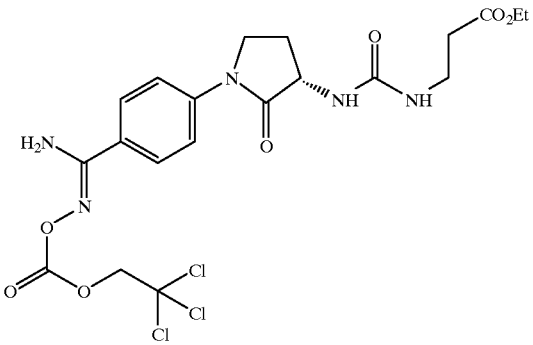

The title compound was prepared from the product of Example 1 (1.05 g, 2.78 mmol) and 2,2,2-trichloroethyl chloroformate (0.59 g, 2.78 mmol) in a manner similar to Example 6 affording the product (1.13 g, 74% yield) after trituration and filtration from ether. (m. p. 196–198° C.).

Analysis calculated for $C_{20}H_{24}N_5O_7Cl_3$: C, 43.46; H, 4.38; N, 12.67. Found: C, 43.17; H, 4.27; N, 12.67.

EXAMPLE 11

Ex Vivo Screening of Oral GP IIb/IIIa Inhibitors

Beagles (8–13 kg, various sources) of either sex are dosed orally with compound in a gelatin capsule. Blood samples are drawn from the cephalic vein using a 23 ga infusion butterfly. Samples for platelet aggregation and drug concentration are taken prior to dosing and 0.5, 1, 2, 3, 5, 7 and 10 hours after dosing and periodically on subsequent days until inhibition of platelet aggregation is less than 30%. Animals are fasted, with ad lib access to water, overnight prior to dosing. For measurement of plasma concentration blood is drawn into a 3 ml tube containing 45 USP units of Na Heparin. Blood is centrifuged at 1700×g for 10 minutes, plasma is aspirated and frozen at −20° C. until analyzed by HPLC. For measurement of platelet aggregation, blood is drawn into 2 2.0 ml tubes containing 0.2 ml of 3.8% Na Citrate. Blood is centrifuged at 250×g for 6 minutes and the platelet rich plasma (PRP) is aspirated. The remaining blood is centrifuged at 1700×g for 10 minutes and platelet poor plasma (PPP) is aspirated. Platelet aggregation is performed in a Bio-Data PAP-4 aggregometer (Bio-Data Corp., Havertown, Pa.) using collagen (100 μg/ml final concentration; Helena Laboratories, Beaumont, Tex.) as the agonist. Briefly, baseline (100% aggregation) is set using PPP; PRP is incubated at 37° C. for one minute without stirring and one minute with stirring, agonist is added and aggregation is allowed to develop for 4 minutes. Percent aggregation post-dosing is compared to percent aggregation pre-dosing to determine percent inhibition. The calculated percent inhibition at 32 hours post-dosing is reported in the following Table 1.

TABLE 1

Percent inhibition of platelet aggregation at 32 hour post-dosing in beagle dogs (5 mpk, n = 2)

| Example # | % inhibition @ 32 hours |
|---|---|
| 1 | 95 |
| 1(a) | 85 |
| 1(b) | 71 |
| 1(c) | 94 |
| 1(d) | 45 |
| 1(f) | 87 |
| 1(h) | 39 |
| 3 | 66 |
| 3(a) | 33% @ 26 hours |
| 3(b) | 54 |
| 3(d) | 88% @ 26 hours |
| 3(e) | 54 |
| 3(f) | 35 |
| 3(g) | 69 |
| 3(h) | 56 |
| 3(j) | 34 |
| 3(l) | 71 |
| 3(m) | 80 |
| 3(n) | 73 |
| 3(q) | 57 |
| 3(r) | 46 |
| 3(u) | 63 |
| 3(cc) | 22 |
| 3(ff) | 70 |
| 4 | 68 |
| 4(a) | 63 |
| 4(b) | 20 |
| 4(c) | 64 |
| 5 | 89 |
| 5(a) | 82 |
| 5(b) | 64 |
| 5(h) | 28 |
| 6(a) | 61% @ 10 hours |
| 6(d) | 15% @ 10 hours |
| 6(e) (RF1) | 28% @ 10 hours |
| 7 | 53 |
| 8 | 57 |
| 9 | 90 |
| 10 | 84 |

EXAMPLE 12

Plasma Concentration Analysis

An HPLC method was employed to determine RF1 concentrations in dog plasma using an appropriate internal standard. The procedure consists of a solid phase extraction of RF1 from dog plasma using a C18 extraction column (100 mg Isolute C18 MF). To 0.25 mL of dog plasma, 0.50 mL of 0.05 N HCl and 100 mL of internal standard solution were added and mixed thoroughly using a vortex mixer. The solid phase extraction process was performed using a Zymark RapidTrace automated extraction system. The C18 column was activated using 1 mL of methanol followed by 1 mL of water. The sample was then loaded into the C18 extraction column and extracted using positive pressure. The C18 extraction column was then washed with 2 mL of water followed by 0.5 mL of acetonitrile. The compounds of interest were then eluted from the C18 extraction column using three 0.5 mL aliquots of 0.2% tetra-ethylammonium phosphate (TEAP) (pH 2.5) and methanol (5:95, by volume). The extract was taken to dryness with nitrogen and reconstituted with HPLC mobile phase A, 10% methanol/ 90% 80 mM ammonium acetate (pH 4.0). The sample was injected onto a reverse phase HPLC.

HPLC analysis was performed on system equipped with a Hewlett-Packard 1050 pump, a Waters 717 autosampler and a Waters Symmetry C18 HPLC column (4.6×100 mm) at 30 degree C. with a Sentry Guard Column Nova-Pak C18 (3.9×20 mm). The analytical run consisted of mobile phase A (10% methanol/90% 80 mM ammonium acetate (pH 4.0)) isocratically for 5 minutes, a linear gradient to mobile phase B (50% or 60% methanol/50% or 40% 80 mM ammonium acetate, pH 4.0) over 10 minutes, a return to mobile A over 5 minutes and a re-equilibration with mobile phase A for 10 more minutes before the next injection. The flow rate was 1.0 mL/minutes. The analyte was quantitated by the peak height ratios to the internal standard using a fluorescent detector at an excitation wavelength of 280 nm and an emission wavelength of 370 nm. The plasma concentrations of RF1 in dog plasma after administration of selected compounds are graphically illustrated in FIG. 1.

What is claimed is:

1. A compound of the formula

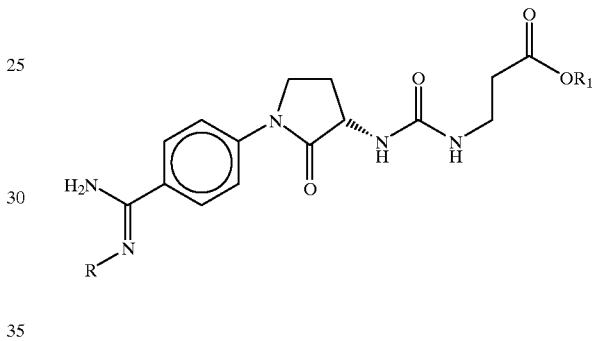

wherein $R_1$ is selected from the group consisting of lower alkyl of about 2 to about 8 carbon atoms, cycloalkyl, and aralkyl; R is selected from the group consisting of alkoxy,

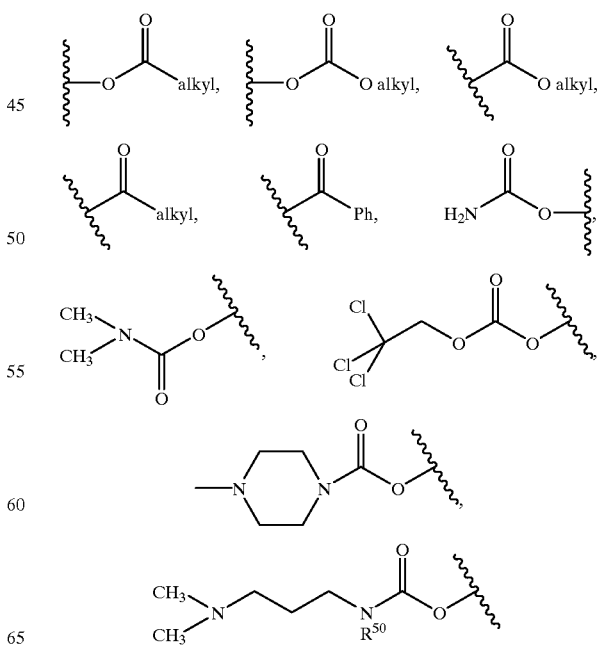

wherein R⁵⁰ is H or alkyl; and

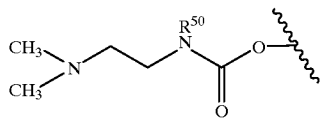

wherein R⁵⁰ is H or alkyl; and pharmaceutically acceptable salts thereof.

2. A compound according to claim 1 selected from the group consisting of

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine methyl ester;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine methyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine methyl ester;

N-[[[(3S)-1-[4-(1-imino-5,9-dimethyl-4-oxo-3-oxa-2,5,9-triazadec-1-yl)-phenyl]-2-oxo-3-pyrrolidinyl]amino]carbonyl]-β-alanine methyl ester;

N-[[[(3S)-1-[4-[imino[[[(4-methyl-1-piperazinyl)carbonyl]oxy]amino]-methyl]phenyl]-2-oxo-3-pyrrolidinyl]amino]carbonyl]-β-alanine ethyl ester;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine ethyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine ethyl ester;

N-[[[(3S)-1-[4-(1-imino-5,9-dimethyl-4-oxo-3-oxa-2,5,9-triazadec-1-yl)-phenyl]-2-oxo-3-pyrrolidinyl]amino]carbonyl]-β-alanine ethyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 1-methylethyl ester;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine 1-methylethyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine 1-methylethyl ester;

N-[[[(3S)-1-[4-(1-imino-5,9-dimethyl-4-oxo-3-oxa-2,5,9-triazadec-1-yl)-phenyl]-2-oxo-3-pyrrolidinyl]amino]carbonyl]-β-alanine 1-methylethyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine propyl ester;

N-[[[(3S)-1-[4-(1-imino-5,8-dimethyl-4-oxo-3-oxa-2,5,8-triazanon-1-yl)-phenyl]-2-oxo-3-pyrrolidinyl]amino]carbonyl]-β-alanine propyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine propyl ester;

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine propyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 2-methylpropyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 2-methylpropyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine 2-methylpropyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 2-methylpropyl ester;

N-[[[(3S)-1-[4-(1-imino-8-methyl-4-oxo-3-oxa-2,5,8-triazanon-1-yl)-phenyl]-2-oxo-3-pyrrolidinyl]amino]carbonyl]-β-alanine 2-methylpropyl ester;

N-[[[(3S)-1-[4-(1-imino-5,9-dimethyl-4-oxo-3-oxa-2,5,9-triazadec-1-yl)phenyl]-2-oxo-3-pyrrolidinyl]amino]carbonyl]-β-alanine 2-methylpropyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine butyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine butyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine butyl ester;

N-[[[(3S)-1-[4-[imino[[[(4-methyl-1-piperazinyl)carbonyl]oxy]amino]methyl]-phenyl]-2-oxo-3-pyrrolidinyl]amino]carbonyl]-β-alanine 2,2-dimethylpropyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine 2,2-dimethylpropyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine 2,2-dimethylpropyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine phenylmethyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine phenylmethyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine phenylmethyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine cyclohexyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine cyclohexyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine cyclohexyl ester;

N-[[[(3S)-1-[4-[imino[[[(4-methyl-1-piperazinyl)carbonyl]oxy]amino]methyl]phenyl]-2-oxo-3-pyrrolidinyl]amino]carbonyl]-β-alanine pentyl ester;

N-[[[(3S)-1-[4-(1-imino-5,8-dimethyl-4-oxo-3-oxa-2,5,8-triazanon-1-yl)phenyl]-2-oxo-3-pyrrolidinyl]amino]carbonyl]-β-alanine pentyl ester;

N-[[[(3S)-1-[4-(1-imino-8-methyl-4-oxo-3-oxa-2,5,8-triazanon-1-yl)phenyl]-2-oxo-3-pyrrolidinyl]amino]carbonyl]-β-alanine pentyl ester;

N-[[[(3S)-1-[4-[imino[[[(4-methyl-1-piperazinyl)
carbonyl]oxy]amino]methyl]phenyl]-2-oxo-3-
pyrrolidinyl]amino]carbonyl]-β-alanine 1,1-
dimethylethyl ester;

N-[[[(3S)-1-[4-(1-imino-5,8-dimethyl-4-oxo-3-oxa-2,5,
8-triazanon-1-yl)phenyl]-2-oxo-3-pyrrolidinyl]amino]
carbonyl]-β-alanine 1,1-dimethylethyl ester;

N-[[[(3S)-1-[4-(1-imino-8-methyl-4-oxo-3-oxa-2,5,8-
triazanon-1-yl)phenyl]-2-oxo-3-pyrrolidinyl]amino]
carbonyl]-β-alanine 1,1dimethylethyl ester;

N-[[[(3S)-1-[4-[[[(dimethylamino)carbonyl]oxy]amino]
imino-methyl]phenyl]-2-oxo-3-pyrrolidinyl]amino]
carbonyl]-β-alanine methyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine ethyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine 1-methylethyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine propyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine 2-methylpropyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine butyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine 2,2-methylpropyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine phenylmethyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine pentyl ester;

N-[[[(3S)-1-[4-[[[(dimethylamino)carbonyl]oxy]amino]
iminomethyl]phenyl]-2-oxo-3-pyrrolidinyl]amino]
carbonyl]-β-alanine 1,1-dimethylethyl ester;

N-[[[(3S)-1-[4-[[[(aminocarbonyl)oxy]amino]
iminomethyl]-phenyl]-2-oxo-3-pyrrolidinyl]amino]
carbonyl]-β-alanine methyl ester;

N-[[[(3S)-1-[4-[[[(aminocarbonyl)oxy]amino]
iminomethyl]phenyl]-2-oxo-3-pyrrolidinyl]amino]
carbonyl]-β-alanine ethyl ester;

N-[[[(3S)-1-[4-[[[(aminocarbonyl)oxy]amino]
iminomethyl]phenyl]-2-oxo-3-pyrrolidinyl]amino]
carbonyl]-β-alanine 1-methylethyl ester;

N-[[[(3S)-1-[4-[[[(aminocarbonyl)oxy]amino]
iminomethyl]phenyl]-2-oxo-3-pyrrolidinyl]amino]
carbonyl]-β-alanine propyl ester;

N-[[[(3S)-1-[4-[[[(aminocarbonyl)oxy]amino]
iminomethyl]phenyl]-2-oxo-3-pyrrolidinyl]amino]
carbonyl]-β-alanine 2-methylpropyl ester;

N-[[[(3S)-1-[4-[[[(aminocarbonyl)oxy]amino]
iminomethyl]phenyl]-2-oxo-3-pyrrolidinyl]amino]
carbonyl]-β-alanine propyl ester;

N-[[[(3S)-1-[4-[[[(aminocarbonyl)oxy]amino]
iminomethyl]phenyl]-2-oxo-3-pyrrolidinyl]amino]
carbonyl]-β-alanine butyl ester;

N-[[[(3S)-1-[4-[[[(aminocarbonyl)oxy]amino]
iminomethyl]phenyl]-2-oxo-3-pyrrolidinyl]amino]
carbonyl]-β-alanine 2,2-dimethylpropyl ester;

N-[[[(3S)-1-[4-[[[(aminocarbonyl)oxy]amino]
iminomethyl]phenyl]-2-oxo-3-pyrrolidinyl]amino]
carbonyl]-β-alanine phenylmethyl ester;

N-[[[(3S)-1-[4-[[[(aminocarbonyl)oxy]amino]
iminomethyl]phenyl]-2-oxo-3-pyrrolidinyl]amino]
carbonyl]-β-alanine cyclohexyl ester;

N-[[[(3S)-1-[4-[[[(aminocarbonyl)oxy]amino]
iminomethyl]phenyl]-2-oxo-3-pyrrolidinyl]amino]
carbonyl]-β-alanine pentyl ester;

N-[[[(3S)-1-[4-[[[(aminocarbonyl)oxy]amino]
iminomethyl]phenyl]-2-oxo-3-pyrrolidinyl]amino]
carbonyl]-β-alanine 1,1-dimethylethyl ester;

N-[[[(3S)-1-[4-[imino[[[(4-methyl-1-piperazinyl)
carbonyl]oxy]amino]methyl]phenyl]-2-oxo-3-
pyrrolidinyl]amino]carbonyl]-β-alanine;

N-[[[(3S)-1-[4-(1-imino-5,8-dimethyl-4-oxo-3-oxa-2,5,
8-triazanon-1-yl)-phenyl]-2-oxo-3-pyrrolidinyl]amino]
carbonyl]-β-alanine;

N-[[[(3S)-1-[4-(1-imino-8-methyl-4-oxo-3-oxa-2,5,
8triazanon-1-yl)phenyl]-2-oxo-3-pyrrolidinyl]amino]
carbonyl]-β-alanine;

N-[[[(3S)-1-[4-[[[(dimethylamino)carbonyl]oxy]amino]
iminomethyl]phenyl]-2-oxo-3-pyrrolidinyl]amino]
carbonyl]-β-alanine;

N-[[[(3S)-1-[4-[[[(aminocarbonyl)oxy]amino]
iminomethyl]phenyl]-2-oxo-3-pyrrolidinyl]amino]
carbonyl]-β-alanine;

N-[[[(3S)-1-[4-[imino[(phenylcarbonyl)amino]methyl]
phenyl]-2-oxo-3-pyrrolidinyl]amino]carbonyl]-β-
alanine ethyl ester;

N-[[[(3S)-1-[4-[imino[(methoxycarbonyl)amino]methyl]
phenyl]-2-oxo-3-pyrrolidinyl]amino]carbonyl]-β-
alanine methyl ester;

N-[[[(3S)-1-[4-[[(acetyloxy)amino]iminomethyl]phenyl]-
2-oxo-3-pyrrolidinyl]amino]carbonyl]-β-alanine ethyl
ester;

N-[[[(3S)-1-[4-[[[(ethoxycarbonyl)oxy]amino]imino-
methyl]phenyl]-2-oxo-3-pyrrolidinyl]amino]
carbonyl]-β-alanine ethyl ester; and N-[[[(3S)-1-[4-[imino[[[(2,2,2-trichloroethoxy)carbonyl]
oxy]amino]methyl]phenyl]-2-oxo-3-pyrrolidinyl]
amino]carbonyl]-β-alanine ethyl ester.

3. A pharmaceutical composition comprising a therapeutically effective amount of a compound according to claim 1 and a pharmaceutically acceptable carrier.

4. A pharmaceutical composition comprising a therapeutically effective amount of a compound according to claim 2 and a pharmaceutically acceptable carrier.

5. A pharmaceutical composition comprising a therapeutically effective amount of a compound selected from the group consisting of:

N-[[[(3S)-1-[4-[(hydroxyamino)iminomethyl]phenyl]-2-
oxo-3-pyrrolidinyl]amino]carbonyl]-β-alanine ethyl
ester;

N-[[[(3S)-1-[4-[(hydroxyamino)iminomethyl]phenyl]-2-
oxo-3-pyrrolidinyl]amino]carbonyl]-β-alanine methyl
ester;

N-[[[(3S)-1-[4-[(hydroxyamino)iminomethyl]phenyl]-2-
oxo-3-pyrrolidinyl]amino]carbonyl]-β-alanine
1-methylethyl ester;

N-[[[(3S)-1-[4-[(hydroxyamino)iminomethyl]phenyl]-2-
oxo-3-pyrrolidinyl]amino]carbonyl]-β-alanine propyl
ester;

N-[[[(3S)-1-[4-[(hydroxyamino)iminomethyl]phenyl]-2-
oxo-3-pyrrolidinyl]amino]carbonyl]-β-alanine
2-methylpropyl ester;

N-[[[(3S)-1-[4-[(hydroxyamino)iminomethyl]phenyl]-2-oxo-3-pyrrolidinyl]amino]carbonyl]-β-alanine butyl ester;

N-[[[(3S)-1-[4-[(hydroxyamino)iminomethyl]phenyl]-2-oxo-3-pyrrolidinyl]amino]carbonyl]-β-alanine 2,2-dimethylpropyl ester;

N-[[[(3S)-1-[4-[(hydroxyamino)iminomethyl]phenyl]-2-oxo-3-pyrrolidinyl]amino]carbonyl]-β-alanine phenylmethyl ester;

N-[[[(3S)-1-[4-[(hydroxyamino)iminomethyl]phenyl]-2-oxo-3-pyrrolidinyl]amino]carbonyl]-β-alanine pentyl ester;

N-[[[(3S)-1-[4-[(hydroxyamino)iminomethyl]phenyl]-2-oxo-3-pyrrolidinyl]amino]carbonyl]-β-alanine 1,1-dimethylethyl ester;

or a pharmaceutically acceptable salt thereof and a pharmaceutically therapeutic carrier.

6. A method of inhibiting platelet aggregation in a mammal in need of such treatment comprising administering a therapeutically effective amount of a compound of a formula according to claim 1.

7. A method of inhibiting platelet aggregation in a mammal in need of such treatment comprising administering a therapeutically effective amount of a compound of a formula according to claim 2.

8. A method of inhibiting platelet aggregation in a mammal in need of such treatment comprising administering a therapeutically effective amount of a compound selected from the group consisting of:

N-[[[(3S)-1-[4-[(hydroxyamino)iminomethyl]phenyl]-2-oxo-3-pyrrolidinyl]amino]carbonyl]-β-alanine ethyl ester;

N-[[[(3S)-1-[4-[(hydroxyamino)iminomethyl]phenyl]-2-oxo-3-pyrrolidinyl]amino]carbonyl]-β-alanine methyl ester;

N-[[[(3S)-1-[4-[(hydroxyamino)iminomethyl]phenyl]-2-oxo-3-pyrrolidinyl]amino]carbonyl]-β-alanine 1-methylethyl ester;

N-[[[(3S)-1-[4-[(hydroxyamino)iminomethyl]phenyl]-2-oxo-3-pyrrolidinyl]amino]carbonyl]-β-alanine propyl ester;

N-[[[(3S)-1-[4-[(hydroxyamino)iminomethyl]phenyl]-2-oxo-3-pyrrolidinyl]amino]carbonyl]-β-alanine 2-methylpropyl ester;

N-[[[(3S)-1-[4-[(hydroxyamino)iminomethyl]phenyl]-2-oxo-3-pyrrolidinyl]amino]carbonyl]-β-alanine butyl ester;

N-[[[(3S)-1-[4-[(hydroxyamino)iminomethyl]phenyl]-2-oxo-3-pyrrolidinyl]amino]carbonyl]-β-alanine 2,2-dimethylpropyl ester;

N-[[[(3S)-1-[4-[(hydroxyamino)iminomethyl]phenyl]-2-oxo-3-pyrrolidinyl]amino]carbonyl]-β-alanine phenylmethyl ester;

N-[[[(3S)-1-[4-[(hydroxyamino)iminomethyl]phenyl]-2-oxo-3-pyrrolidinyl]amino]carbonyl]-β-alanine pentyl ester;

N-[[[(3S)-1-[4-[(hydroxyamino)iminomethyl]phenyl]-2-oxo-3-pyrrolidinyl]amino]carbonyl]-β-alanine 1,1-dimethylethyl ester;

or a pharmaceutically acceptable salt thereof.

* * * * *